US012642966B2

(12) United States Patent
Srivastava et al.

(10) Patent No.: US 12,642,966 B2
(45) Date of Patent: Jun. 2, 2026

(54) GOAL SETTING AND TRACKING FOR NEUROMODULATION TREATMENT

(71) Applicant: Boston Scientific Neuromodulation Corporation, Valencia, CA (US)

(72) Inventors: Kyle Harish Srivastava, Saint Paul, MN (US); Amarpreet Singh Bains, Woodbury, MN (US); Benjamin Phillip Hahn, Austin, TX (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 269 days.

(21) Appl. No.: 18/380,535

(22) Filed: Oct. 16, 2023

(65) Prior Publication Data

US 2024/0131337 A1 Apr. 25, 2024
US 2024/0226560 A9 Jul. 11, 2024

Related U.S. Application Data

(60) Provisional application No. 63/417,810, filed on Oct. 20, 2022.

(51) Int. Cl.
*A61N 1/36* (2006.01)
*A61N 1/372* (2006.01)
(Continued)

(52) U.S. Cl.
CPC ..... *A61N 1/36071* (2013.01); *A61N 1/36139* (2013.01); *A61N 1/37247* (2013.01);
(Continued)

(58) Field of Classification Search
CPC ........... A61N 1/36071; A61N 1/36139; G16H 20/30; G16H 40/67
(Continued)

(56) References Cited

U.S. PATENT DOCUMENTS 9,364,679 B2    6/2016   John
2011/0172744 A1    7/2011   Davis et al.
(Continued)

FOREIGN PATENT DOCUMENTS

WO    WO-2021141652 A1    7/2021
WO    WO-2024086103 A1    4/2024

OTHER PUBLICATIONS

"International Application Serial No. PCT/US2023/035215, International Preliminary Report on Patentability mailed May 1, 2025", 7 pgs.
(Continued)

*Primary Examiner* — Nadia A Mahmood
(74) *Attorney, Agent, or Firm* — Schwegman Lundberg & Woessner, P.A.

(57) ABSTRACT

Systems, devices, and methods are disclosed for computer-assisted goal setting and tracking with respect to neuro-modulation device treatment. A digital health system includes a user-interface device to receive a user input about a personalized objective of neuromodulation treatment or an intended manner of using the neuromodulation device by the patient. The user input can be in forms of text, voice, or other unstructured or unclassified data formats. A controller circuit can process the user input using analytical methods including natural language processing to generate a personalized treatment and device usage goal, and track the progress toward the personalized treatment and device usage goal using patient state information. The tracked progress may be presented to the patient, or be used to initiate or adjust a neuromodulation therapy.

20 Claims, 12 Drawing Sheets

(51) Int. Cl.
    *G16H 20/30*        (2018.01)
    *G16H 40/67*        (2018.01)

(52) U.S. Cl.
    CPC ..... *A61N 1/37258* (2013.01); *A61N 1/37264*
        (2013.01); *G16H 20/30* (2018.01); *G16H*
                           *40/67* (2018.01)

(58) Field of Classification Search
    USPC .......................................................... 607/46
    See application file for complete search history.

(56) References Cited

U.S. PATENT DOCUMENTS

| | | |
|---|---|---|
| 2015/0039047 A1 | 2/2015 | Parker |
| 2018/0085580 A1 | 3/2018 | Perez et al. |
| 2020/0282218 A1 | 9/2020 | McDonald |
| 2022/0134117 A1 | 5/2022 | Woock et al. |
| 2022/0134119 A1 | 5/2022 | Mcdonald et al. |
| 2022/0143403 A1* | 5/2022 | Offutt ................ A61N 1/36007 |
| 2023/0181109 A1 | 6/2023 | Srivastava et al. |

OTHER PUBLICATIONS

"International Application Serial No. PCT/US2023/035215, International Search Report mailed Feb. 8, 2024", 4 pgs.
"International Application Serial No. PCT/US2023/035215, Written Opinion mailed Feb. 8, 2024", 5 pgs.

* cited by examiner

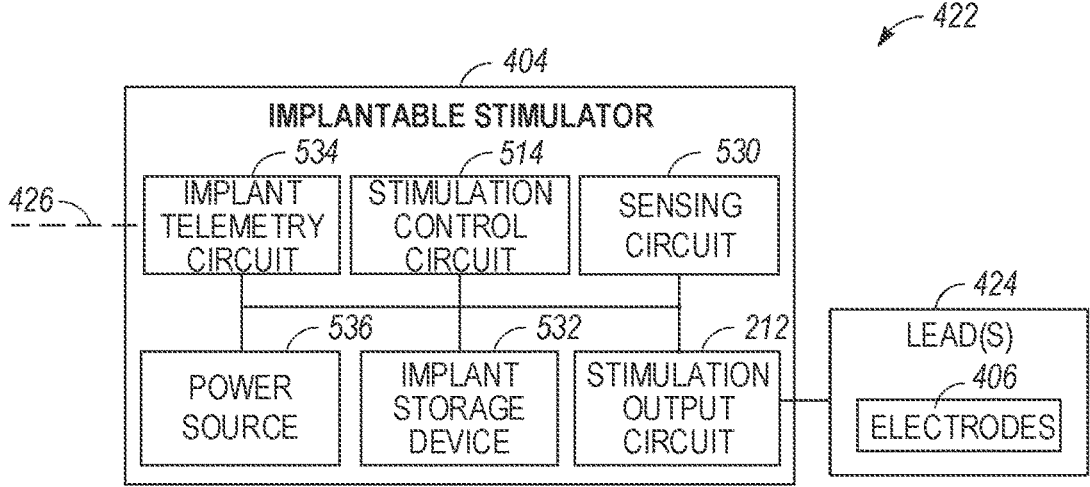

— 422

IMPLANTABLE STIMULATOR — 404

534 IMPLANT TELEMETRY CIRCUIT

514 STIMULATION CONTROL CIRCUIT

530 SENSING CIRCUIT

426 —

536 POWER SOURCE

532 IMPLANT STORAGE DEVICE

212 STIMULATION OUTPUT CIRCUIT

424 LEAD(S)

406 ELECTRODES

PROGRAMMING SYSTEM

610 USER INTERFACE

612 DISPLAY SCREEN

614 USER INPUT DEVICE

620 PROGRAMMING CONTROL CIRCUIT

640 EXTERNAL TELEMETRY CIRCUIT

— 426

622 NEUROSTIMULATION PARAMETER SELECTION CIRCUIT

630 CONTROLLER

616 EXTERNAL STORAGE DEVICE

618 EXTERNAL COMMUNICATION DEVICE

DATA ANALYSIS COMPUTING SYSTEM — 650

660 TREATMENT ACTION CIRCUITRY

662 PATIENT OUTPUT CIRCUITRY

664 CLINICIAN OUTPUT CIRCUITRY

652 DEVICE DATA PROCESSING CIRCUIT

654 TEXT PROCESSING CIRCUIT

656 STORAGE DEVICE

FIG. 6

GOAL SETTING AND TRACKING FOR NEUROMODULATION TREATMENT

CLAIM OF PRIORITY

This application claims the benefit of U.S. Provisional Application No. 63/417,810, filed on Oct. 20, 2022, which is hereby incorporated by reference in its entirety.

TECHNICAL FIELD

The present disclosure relates generally to medical devices, and more particularly, to systems, devices, and methods for setting and tracking a personalized goal of neuromodulation device treatment.

BACKGROUND

Chronic pain, such as pain present most of the time for a period of six months or longer during the prior year, is a highly pervasive complaint and consistently associated with psychological illness. Chronic pain may originate with a trauma, injury or infection, or there may be an ongoing cause of pain. Chronic pain may also present in the absence of any past injury or evidence of body damage. Common chronic pain can include headache, low back pain, cancer pain, arthritis pain, neurogenic pain (pain resulting from damage to the peripheral nerves or to the central nervous system), or psychogenic pain (pain not due to past disease or injury or any visible sign of damage inside or outside the nervous system Neurostimulation, also referred to as neuromodulation, has been proposed as a therapy for a number of conditions including chronic pain. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system.

A neurostimulation system has been used to electrically stimulate tissue or nerve centers to treat nervous or muscular disorders. For example, an SCS system may be configured to deliver electrical pulses to a specified region of a patient's spinal cord, such as particular spinal nerve roots or nerve bundles, to produce an analgesic effect that masks pain sensation, or to produce a functional effect that allows increased movement or activity of the patient. Other forms of neurostimulation may include a DBS system which uses similar pulses of electricity at particular locations in the brain to reduce symptoms of essential tremors, Parkinson's disease, psychological disorders, or the like.

The capability of a neurostimulation system largely depends on its programmability. Neurostimulation systems are typically programmed by a clinician or a system expert in a clinical setting using a clinical programmer. For example, a clinician may use the clinical programmer to set one or more stimulation parameters (e.g., pulse voltage or current amplitude, pulse width, or pulse rate), select an electrostimulation program (as defined by a group of parameter values) for an electrical stimulation therapy to be delivered to the patient, or program active electrodes to deliver the electrostimulation pulses. The clinical programmer may also allow the clinician to set a neuromodulation device treatment goal for the patient.

Some neurostimulation systems include a patient programmer that enables a patient to interact with his or her neuromodulation device (also referred to as "neurostimulation device"), such as activating or deactivating a neurostimulation therapy, changing a stimulation parameter value, or switching between stimulation programs, among other adjustments of device settings. The patient programmer allows the patients to directly tune the neurostimulation therapy to meet personal needs in an ambulatory setting without frequent clinic visits.

For patients receiving neuromodulation device treatment for chronic pain, adequate pain relief is the most common treatment goal. However, such patients usually have other goals related to functional, emotional, and social wellness and improved quality-of-life measures. Devices and techniques to assist the patient in setting personalized treatment goals and automatically tracking the progress toward the set goal are desired to help the patient actively monitor their treatment and achieve the treatment goal.

SUMMARY

This document discusses systems, devices, and methods for computer-assisted goal setting and tracking in relation to neuromodulation device treatment of chronic pain or other medical conditions. According to one embodiment, a digital health system can include a user-interface device to receive a user input about a personalized objective of neuromodulation treatment for the patient or an intended manner of using the neuromodulation device by the patient. The user input can be in forms of freeform text, voice, or other unstructured or unclassified data formats. The system includes a controller circuit that can process the user input using analytical methods such as natural language processing, generate a personalized treatment and device usage goal, and track the progress toward the personalized treatment and device usage goal using patient physiological or functional information or a user feedback on the execution of the personalized treatment and device usage goal. The tracked progress may be presented to the patient or an authorized user, or used by the controller circuit to initiate or adjust a neuromodulation therapy.

Example 1 is a system for monitoring neuromodulation device treatment progress of a patient. The system comprises: a user-interface device; and a controller circuit configured to: receive from the user-interface device a user input about (i) a personalized objective of neuromodulation treatment for the patient or (ii) an intended manner of using a neuromodulation device by the patient; process the received user input to generate a personalized treatment and device usage goal; track progress toward the personalized treatment and device usage goal based on patient state information; and generate a control signal to the neuromodulation device to initiate or adjust a neuromodulation therapy based on the tracked progress toward the personalized treatment and device usage goal.

In Example 2, the subject matter of Example 1 optionally includes, wherein the user input includes text or voice input, and wherein to generate the personalized treatment and device usage goal, the controller circuit is configured to process the text or voice input using natural language processing, and to generate the personalized treatment and device usage goal based on the processed text or voice input.

In Example 3, the subject matter of Example 2 optionally includes, wherein to generate the personalized treatment and device usage goal, the controller circuit is configured to determine a goal type using topic modeling of the text or voice input, and to generate a performance metric for the determined goal type.

In Example 4, the subject matter of Example 3 optionally includes, wherein the controller circuit is configured to evaluate the performance metric using the patient state information, and to track the progress toward the personalized treatment and device usage goal based on the evaluation of the performance metric.

In Example 5, the subject matter of Example 4 optionally includes, wherein the controller circuit is configured to determine that the patient is on track, off track, or has achieved the personalized treatment and device usage goal based on a comparison between the evaluated performance metric and the personalized treatment and device usage goal.

In Example 6, the subject matter of Example 5 optionally includes, wherein, in response to the determination that the patient is on track, the controller circuit is configured to: identify a neuromodulation treatment or patient activities correlated to the determination of the patient being on track; and present information about the identified neuromodulation treatment or the patient activities on the user-interface device.

In Example 7, the subject matter of any one or more of Examples 5-6 optionally include, wherein, in response to the determination that the patient is off track, the controller circuit is configured to: generate an alert to the patient; and automatically modify or prompt the patient to modify the personalized treatment and device usage goal or to adjust the neuromodulation therapy.

In Example 8, the subject matter of any one or more of Examples 5-7 optionally include, wherein, in response to the determination that the patient has achieved the personalized treatment and device usage goal, the controller circuit is configured to automatically generate or prompt the user to provide another goal different than the personalized treatment and device usage goal that has been achieved.

In Example 9, the subject matter of any one or more of Examples 1-8 optionally include, wherein the patient state information includes physiological or functional information collected from the patient by one or more sensors.

In Example 10, the subject matter of any one or more of Examples 1-9 optionally include, wherein the patient state information includes a user feedback including text or voice feedback on execution of the personalized treatment and device usage goal via the user-interface device, and wherein the controller circuit is configured to process the text or voice feedback using natural language processing, and to track the progress toward the personalized treatment and device usage goal based on the processed text or voice feedback.

In Example 11, the subject matter of any one or more of Examples 1-10 optionally include, wherein the controller circuit is configured to generate or modify the personalized treatment and device usage goal further using historical data of the patient in relation to historical neuromodulation treatments and patient responses thereto or historical manners of operating the neuromodulation device.

In Example 12, the subject matter of Example 11 optionally includes a communication circuit configured to receive the historical data of the patient from the neuromodulation device or a wearable tracking device.

In Example 13, the subject matter of any one or more of Examples 1-12 optionally include, wherein the controller circuit is configured to generate or modify the personalized treatment and device usage goal further using population-based data collected from a plurality of individuals having similar medical conditions or similar demographics to the patient, the population-based data in relation to neuromodulation treatments and patient responses thereto or manners of operating respective neuromodulation devices.

In Example 14, the subject matter of any one or more of Examples 1-13 optionally include, wherein the personalized treatment and device usage goal includes at least one of: a mobility goal; a sleep goal; a pain relief goal; or an emotion goal.

In Example 15, the subject matter of any one or more of Examples 1-14 optionally include, wherein the personalized treatment and device usage goal includes at least one of: a device charging schedule or frequency; or a power usage mode of the neuromodulation device.

Example 16 is a method of monitoring neuromodulation device treatment progress in a patient. The method comprises steps of: receiving from a user-interface device a user input about (i) a personalized objective of neuromodulation treatment for the patient or (ii) an intended manner of using the neuromodulation device by the patient; generating, via a controller circuit, a personalized treatment and device usage goal using the received user input; tracking, via the controller circuit, progress toward the personalized treatment and device usage goal based on patient state information; and initiating or adjusting a neuromodulation therapy via the neuromodulation device based on the tracked progress toward the personalized treatment and device usage goal.

In Example 17, the subject matter of Example 16 optionally includes, wherein the user input includes text or voice input, wherein generating the personalized treatment and device usage goal includes processing the text or voice input using natural language processing, and generating the personalized treatment and device usage goal based on the processed text or voice input.

In Example 18, the subject matter of Example 17 optionally includes, wherein generating the personalized treatment and device usage goal includes determining a goal type using topic modeling of the text or voice input, and generating a performance metric for the determined goal type.

In Example 19, the subject matter of Example 18 optionally includes evaluating the performance metric using the patient state information, wherein tracking the progress toward the personalized treatment and device usage goal is based on the evaluation of the performance metric.

In Example 20, the subject matter of Example 19 optionally includes determining that the patient is on track, off track, or has achieved the personalized treatment and device usage goal based on a comparison between the evaluated performance metric and the personalized treatment and device usage goal.

In Example 21, the subject matter of any one or more of Examples 16-20 optionally include, wherein the patient state information used for tracking the progress toward the personalized treatment and device usage goal includes at least one of physiological or functional information of the patient collected by one or more sensors, or a text or voice feedback on execution of the personalized treatment and device usage goal provided by a user via the user-interface device.

In Example 22, the subject matter of any one or more of Examples 16-21 optionally include, wherein generating the personalized treatment and device usage goal is further based on at least one of: historical data of the patient in relation to historical neuromodulation treatments and patient responses thereto or historical manners of operating of the neuromodulation device; or population-based data collected from a plurality of individuals having similar medical conditions or similar demographics to the patient, the population-based data in relation to neuromodulation treatments and patient responses thereto or manners of operating respective neuromodulation devices.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 5 illustrates, by way of example and not limitation, an implantable stimulator and one or more leads of a neurostimulation system, such as the implantable neurostimulation system of FIG. 4.

FIG. 6 illustrates, by way of example and not limitation, a programming system and data analysis system for use with a neurostimulation system, such as the implantable neurostimulation system of FIG. 4.

6 device, and various components of a computing system configured to generate and track a personalized treatment and device usage goal.

Figure 9:
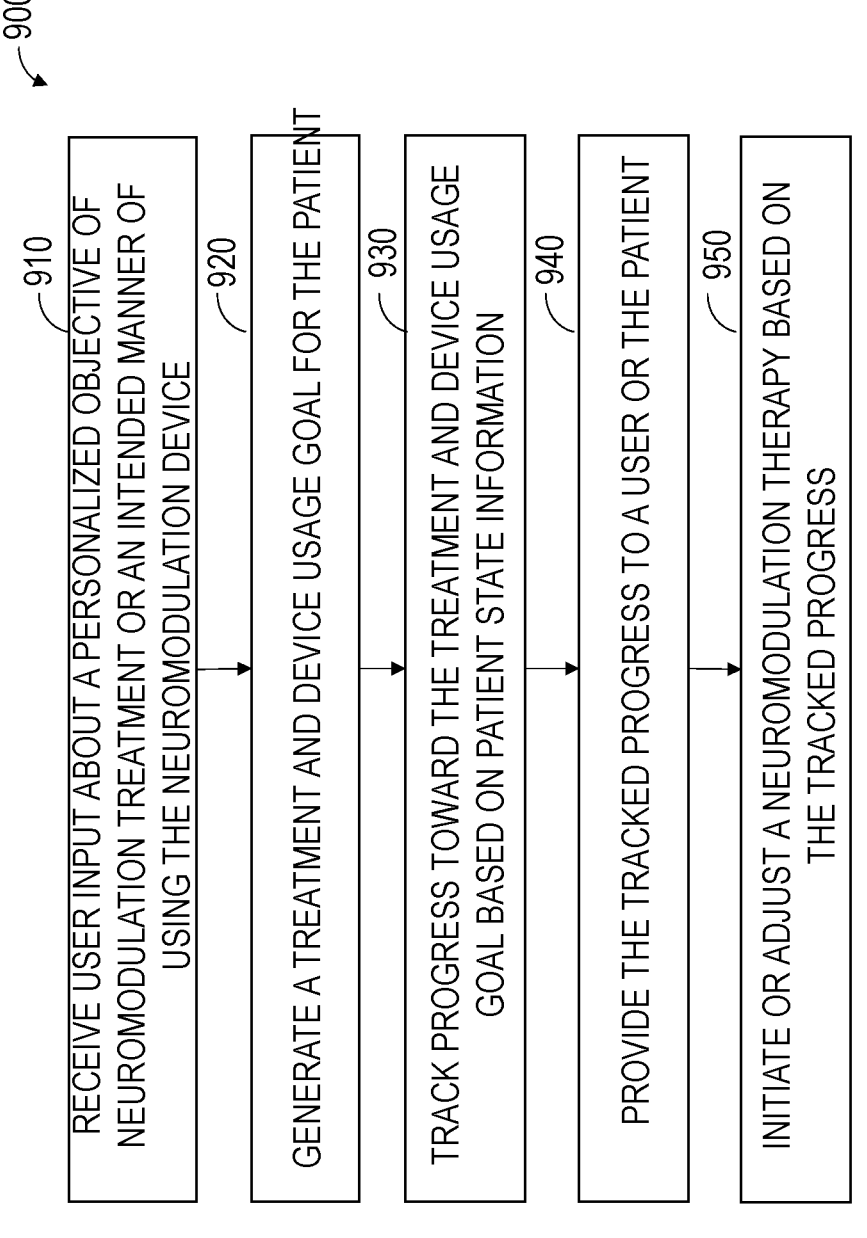

FIG. 9 illustrates, by way of example and not limitation, a method of monitoring neuromodulation device treatment progress in a patient.

Figure 10:
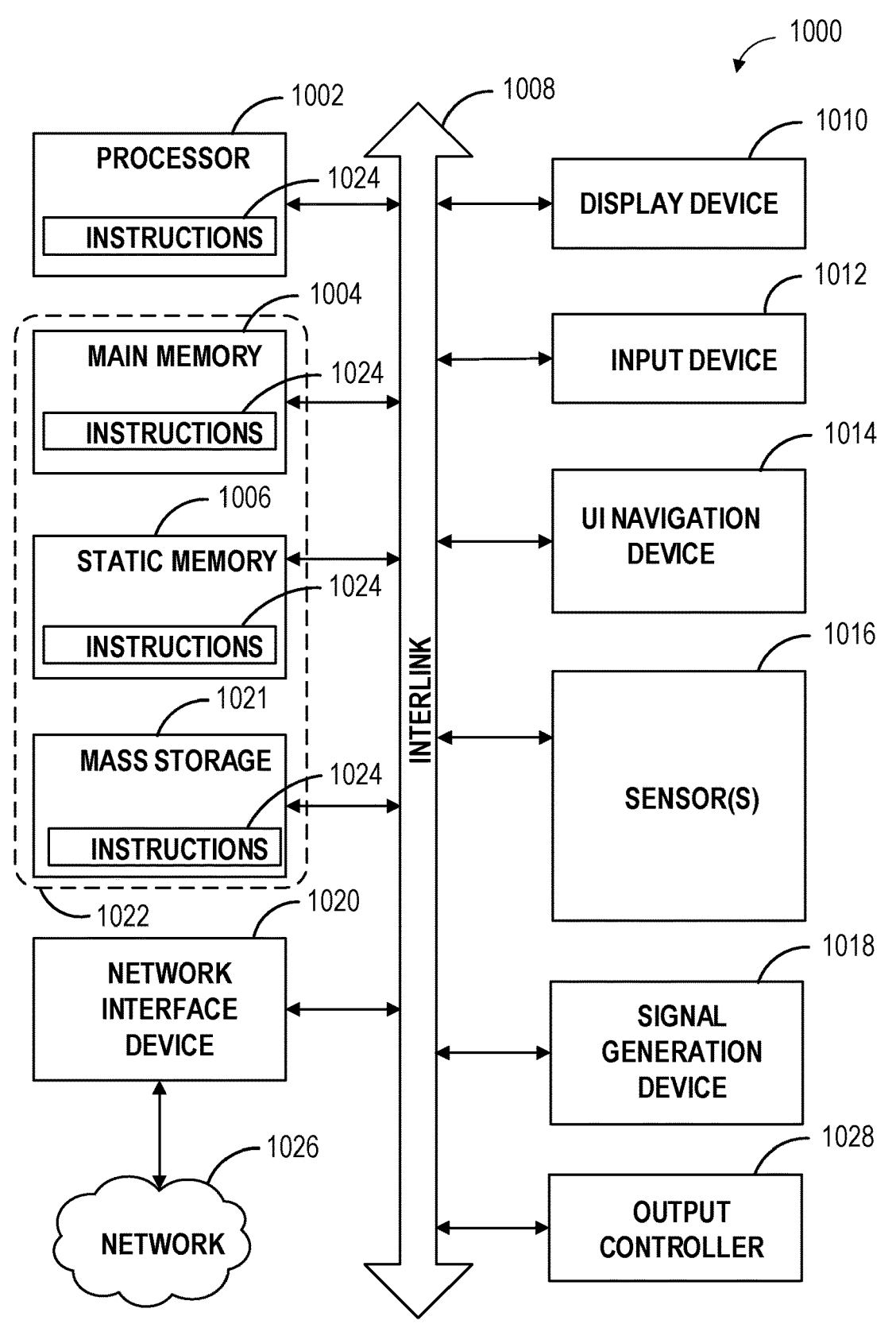

FIG. 10 is a block diagram illustrating generally an example machine upon which any one or more of the techniques (e.g., methodologies) discussed herein may perform.

DETAILED DESCRIPTION

By way of example, chronic pain management may involve monitoring patient pain symptoms and physical, functional, and emotional well-being, determining appropriate treatment options (e.g., neuromodulation therapies with an implantable device), and evaluating patient response to pain therapy. Effective monitoring and accurate pain assessment are important for managing patients with chronic pain. Such assessment may include a pain rating, such as on a numerical scale of 1 to 10 (with 10 being the worst pain) or similar descriptors of pain intensities. Such pain rating, however, may have several drawbacks. For one thing, chronic pain patients may have different tolerances to pain, making the pain ratings subjective and less comparable among patients. Additionally, the pain rating alone may not reflect patient physical and functional capacities. Although chronic pain may limit patient functional capacity and cause mobility issues, an improvement in pain sensation (e.g., a lower pain rating) may not always be accompanied by or synchronized with a progress in the patient's functional capacities, mobility status, and overall quality of life. For example, a chronic pain patient may report a sizable reduction in pain yet remains to be bedridden without gaining improvement in his/her physical or functional capacities. In another example, a chronic pain patient may not report substantial pain reduction, even though he/she has started walking, sleeping normally, and engaging in more activities.

Functional assessment has been performed clinically to optimize function-based strategy for treating chronic pain. A function-based strategy involves measuring a patient's progress not in pain relief (e.g., a decrease in pain rating), but in physical functions such as sleeping, walking, working, connecting with friends, or other behavioral and social activities in daily life. Such functional assessment can provide more objective insight into patient physical and social capacities and quality of life (QoL), and can be used to evaluation an efficacy of a pain therapy (e.g., neuromodulation therapy such as SCS) received by the patient or whether the pain therapy needs to be adjusted.

The goal of neuromodulation treatment in chronic pain patients can vary from controlling or reducing pain to improved functional capabilities, such as improved sleep time and quality or enhanced physical activity capacity. Conventionally such treatment goals are set by clinicians or other healthcare professionals, and are typically evaluated at the doctor's office such as during a follow-up visit. For some patients and on some occasions, such clinician-based, in-person assessment of progress toward the goal in a clinical setting may not always be feasible or practical, and the treatment goal is not frequently assessed. On the hand, some patients with chronic pain and under long-term treatment (e.g., via an implantable neuromodulator) may experience gradual physiological, functional, or emotional changes, which would require their treatment goal to be adjusted accordingly. However, as the patient is outside a clinical setting, such changes in patient conditions can get unnoticed for an extended period of time until it becomes symptomatic, and their treatment goals would not be timely updated.

Conventional clinician-based device management, including therapy programming and treatment goal setting and tracking, generally requires the patient to provide detailed feedback to a clinician in a clinical setting such as during a scheduled doctor's visit. Such patient feedback may be used for setting or updating a treatment goal, or for identifying a treatment issue and titrating a neuromodulation treatment. However, even simple clinician queries such as, "Does the neurostimulation effectively treat your pain?" may be difficult for a patient to answer, especially when evaluating a course of treatment over time that involves multiple stimulation programs. Improved techniques for analyzing text or voice feedback directly from the patient to extract information useable for setting quantifiable treatment goals and for tracking patient progress toward the goal are needed.

The present inventors have recognized that a remotely accessible patient monitoring and pain management platform with enhanced capability of setting a personalized treatment goal and automatically tracking the progress toward the set goal can be more desirable and advantageous in certain situations than a conventional in-person visit at a clinic. Such a patient monitoring and pain management platform can allow a patient to set or update a personalized treatment goal of, for example, reducing pain or improving functional capabilities (e.g., quality sleep or enhanced physical capacity), to monitor patient condition and response to treatment, and to assess a progress toward the treatment goal in their homes between clinic visits. Various techniques described herein can be used to more effectively and efficiently generate personalized treatment goals for patients with different health issues or medical conditions (e.g., chronic pain), or different levels of skills or inclination to engage with their neuromodulation devices. In some examples, a personalized treatment and device usage goal can be generated based on a user input in forms of freeform text, voice, or other unstructured or unclassified data formats. Patient's progress toward the personalized treatment and device usage goal can be automatically tracked using physiological or functional information of the patient or a user feedback on the execution of the personalized treatment and device usage goal. The patient or an authorized user (e.g., a healthcare provider) can be notified about the tracked progress, make adjustment of the goal or tune the neuromodulation treatment to meet the patient's needs.

The patient monitoring and pain management system and methods of using the same in accordance with various embodiments described in this document may improve the technology of device-based pain management. The computer-assisted goal setting and automated goal tracking can help patients and clinicians to better track therapy outcome and optimize treatment outside a clinical setting continuously, periodically, or at any desired time. In various examples, natural language processing (NLP), along with other analytical methods, are used to analyze freeform text or voice input from a patient to accurately and efficiently interpret and extract relevant contents related to patient treatment objectives or responses to treatment. The computer-assisted goal setting can also advantageously drive patient engagement with their neuromodulation devices, enhance their confidence interacting with the device and exploration of device functions or advanced therapy options, and make timely adjustment of therapy or more proactive interactions with their healthcare providers.

In addition to use with aspects of programs and programming values, information from the evaluation of freeform text may also be used to cause device actions (e.g., to run diagnostics on the neuromodulation device). In some examples, information from the evaluation of freeform text may be used to provide informational content to a patient or to a clinician (e.g., to present guidance regarding the effects of treatment or ways to improve treatment outcomes), to provide a clinical triage system, or to update data records, among other effects. For example, based on the evaluation of patient freeform text, voice, or similar forms of unstructured or unclassified data, the systems and methods are described to generate, identify, implement, adjust, or assess parameters of neuromodulation treatment and treatment effects. These systems and methods are further designed to evaluate the current results of neuromodulation treatment, and to determine changes or actions relative to therapy objectives and desired outcomes. As a result, programming modifications, alerts, or other outcomes may be achieved to assist the treatment for a particular patient.

In various embodiments, the present subject matter may be implemented using a combination of hardware and software designed to capture and analyze freeform text, voice, or other unstructured information from users, and related device data or context from a neuromodulation treatment. For instance, some examples are provided with reference to a mobile computing device (e.g., smartphone) app executing a user interface to collect freeform text, entered in the form of questions or voice commands. Other examples are provided with reference to a computing system implemented via a chatbot (e.g., generating data for a smartphone app chat session or SMS message chat session) that presents questions or replies, in an effort to collect and process patient input provided in text (e.g., provided directly in freeform text from a patient response, provided from converted voice-to-text responses, or provided directly or indirectly with other interactions with various parties or entities). Still other examples are provided with reference to a computing system platform which captures and evaluates data from sensors (e.g., wearable devices, implantable devices, or the neuromodulation device) that can be used to cross-reference or correlate freeform text statements from a patient. Many of the following approaches are provided with specific reference to text analysis and NLP, but it will be understood that such approaches may be supplemented or substituted with other technical implementations of text processing and data analysis involving including artificial intelligence (AI), including models implementing machine learning, neural networks, decision trees, and the like.

It will be understood that a variety of the following embodiments may be operated to provide users such as patients, caregivers, clinicians, researchers, physicians, or others with the ability to monitor, collect and provide feedback, and adapt neurostimulation programs and neurostimulation effects (including, neurostimulation programming that provides a variation in the location, intensity, and type of defined waveforms and patterns in an effort to increase therapeutic efficacy and/or patient satisfaction). While neurostimulation therapies, such as SCS and DBS therapies, are specifically discussed as examples, the present subject matter may apply to other therapies that employs stimulation pulses of electrical or other forms of energy for treating chronic pain or like physiological or psychological conditions.

The delivery of neurostimulation energy that is discussed herein may be delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Many current neurostimulation systems are programmed to deliver periodic pulses with one or a few uniform waveforms continuously or in bursts. However, neural signals may include more sophisticated patterns to communicate various types of information, including sensations of pain, pressure, temperature, etc. Accordingly, the following drawings provide an introduction to the features of an example neurostimulation system and how such programming may be accomplished through open-loop or closed-loop neurostimulation systems, and integrated with the present data analysis platforms.

Figure 1:
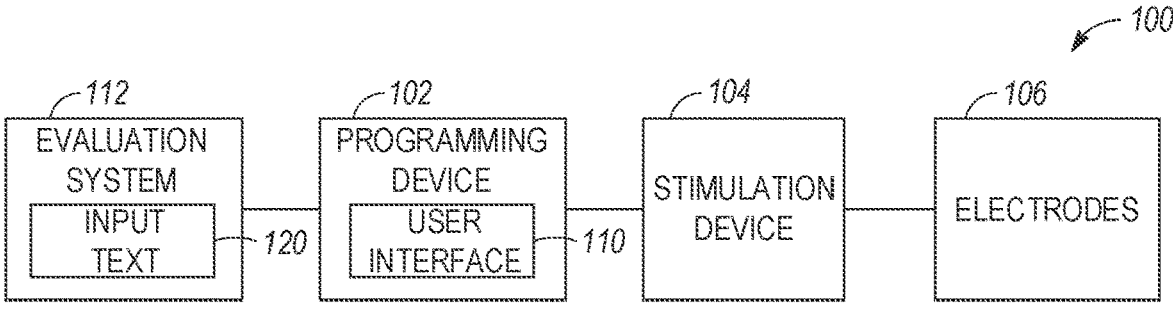
FIG. 1 illustrates, by way of example and not limitation, a neurostimulation system.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are selected or programmable by a clinical user, such as a physician or other caregiver who treats the patient using system 100; however, some of the parameters may also be provided in connection with closed-loop programming logic and adjustment. Programming device 102 provides the user with accessibility to implement, change, or modify the programmable parameters. In various embodiments, programming device 102 is configured to be communicatively coupled to stimulation device 104 via a wired or wireless link.

In various embodiments, programming device 102 includes a user interface 110 (e.g., a user interface embodied by a graphical, text, voice, or hardware-based user interface) that allows the user to set and/or adjust values of the user-programmable parameters by creating, editing, loading, and removing programs that include parameter combinations such as patterns and waveforms. These adjustments may also include changing and editing values for the user-programmable parameters or sets of the user-programmable parameters individually (including values set in response to a therapy efficacy indication). Such waveforms may include, for example, the waveform of a pattern of neurostimulation pulses to be delivered to the patient as well as individual waveforms that are used as building blocks of the pattern of neurostimulation pulses. Examples of such individual waveforms include pulses, pulse groups, and groups of pulse groups. The program and respective sets of parameters may also define an electrode selection specific to each individually defined waveform.

The present approaches further provide examples of an evaluation system 112, such as a data analysis system, which is used to adapt, modify, start, stop, monitor, or identify a neuromodulation treatment with stimulation device 104. The evaluation system 112 can be associated with, or included into, the programming device 102. The evaluation system 112 initiates an action related to the neuromodulation treatment based on text analysis performed on input text 120. The input text 120 can be in forms of freeform text, voice, or other unstructured or unclassified data formats from users. The input text 120 may be directly collected from the patient or an authorized user (such as via the user interface 110 of the programming device 102) and analyzed by the evaluation system 112, to then cause a programming effect in the programming device 102, and the stimulation device 104, and the neuromodulation treatment provided by the electrodes 106. The user input may be used to select, load, modify, implement, measure, analyze, or evaluate one or more parameters of a defined program for neuromodulation treatment that is implemented by the stimulation device 104, or the operation of the stimulation device 104. In some examples, the user input may contain information about patient feedback on treatment (e.g., a therapy program provided by the neuromodulation device). The patient input or feedback may be evaluated using one or more analytical methods including, for example, natural language processing (NLP), sentiment analysis, rules, and other operational or treatment objectives that are identified. Various logic or algorithms can then determine an appropriate action to take based on the state of the patient, including but not limited to: a program or parameter change or recommendation to produce an improvement for a treatment objective (such as to address pain, increase mobility, reduce sleep disruption, and the like); diagnostic or remedial actions on the stimulation device 104; data logging or alerts to the patient or a clinician associated with the patient; and the like.

Example parameters that can be implemented by a selected neurostimulation program include, but are not limited to the following: amplitude, pulse width, frequency, duration, total charge injected per unit time, cycling (e.g., on/off time), pulse shape, number of phases, phase order, interphase time, charge balance, ramping, as well as spatial variance (e.g., electrode configuration changes over time). As detailed in FIG. 6, a controller, e.g., controller circuit 630 of FIG. 6, can implement program(s) and parameter setting(s) to affect a specific neurostimulation waveform, pattern, or energy output, using a program or setting in storage, e.g., external storage device 616 of FIG. 6, or using settings communicated via an external communication device 618 of FIG. 6 corresponding to the selected program. The implementation of such program(s) or setting(s) may further define a therapy strength and treatment type corresponding to a specific pulse group, or a specific group of pulse groups, based on the specific programs or settings. The evaluation system 112 and the evaluation of the input text 120 provide a mechanism to determine the effectiveness of such programs or settings, and to identify issues and provide remediation for ineffective programs or settings, offer suggestions or recommendations for new programs or settings, or even to automatically change programs or settings. The evaluation system 112 and the evaluation of the input text 120 may further be used to set an individualized treatment and device usage goal, and to evaluate the patient's progress toward said treatment and device usage goal.

Portions of the evaluation system 112, the stimulation device 104 (e.g., implantable medical device), or the programming device 102 can be implemented using hardware, software, or any combination of hardware and software. Portions of the stimulation device 104 or the programming device 102 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller circuit or a portion thereof, or a programmable logic circuit, or a portion thereof. The system 100 could also include a subcutaneous medical device (e.g., subcutaneous ICD, subcutaneous diagnostic device), wearable medical devices (e.g., patch-based sensing device), or other external medical devices.

Figure 2:
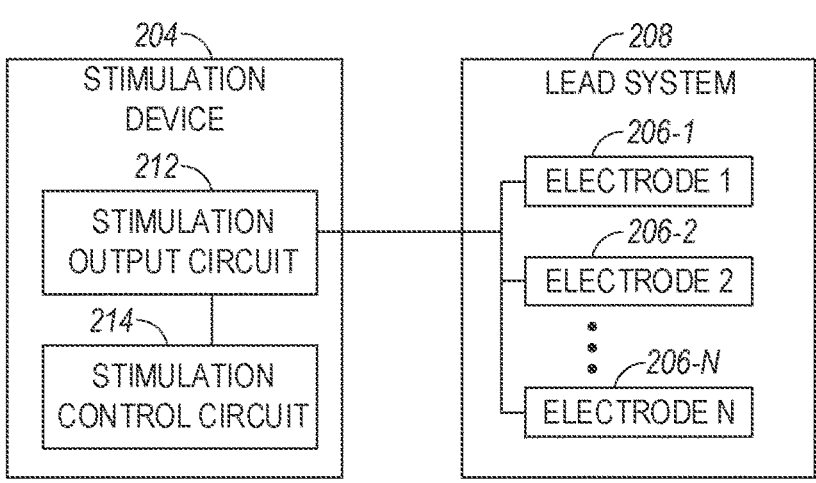
FIG. 2 illustrates, by way of example and not limitation, a stimulation device and a lead system, such as may be implemented in the neurostimulation system of FIG. 1.

FIG. 2 illustrates an embodiment of a stimulation device 204 and a lead system 208, such as may be implemented in neurostimulation system 100 of FIG. 1. Stimulation device 204 represents an embodiment of stimulation device 104 and includes a stimulation output circuit 212 and a stimulation control circuit 214. Stimulation output circuit 212 produces and delivers neurostimulation pulses, including the neurostimulation waveform and parameter settings implemented via a program selected or implemented with the user interface 110. Stimulation control circuit 214 controls the delivery of the neurostimulation pulses using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes. Those of ordinary skill in the art will understand that the neurostimulation system 100 may include additional components such as sensing circuitry for patient monitoring and/or feedback control of the therapy, telemetry circuitry, and power. The neurostimulation system 100 may also integrate with other sensors, or such other sensors may independently provide information for use with programming of the neurostimulation system 100.

The neurostimulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "modulation parameter" set. Each set of modulation parameters, including fractionalized current distribution to the electrodes (as percentage cathodic current, percentage anodic current, or off), may be stored and combined into a program that can then be used to modulate multiple regions within the patient.

The neurostimulation system may be configured to deliver different electrical fields to achieve a temporal summation of modulation. The electrical fields can be generated respectively on a pulse-by-pulse basis. For example, a first elec-trical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields can be rotated or cycled through multiple times under a timing scheme, where each field is implemented using a timing channel. The electrical fields may be generated at a continuous pulse rate, or as bursts of pulses. Furthermore, the interpulse interval (i.e., the time between adjacent pulses), pulse amplitude, and pulse duration during the electrical field cycles may be uniform or may vary within the electrical field cycle. Some examples are configured to determine a modulation parameter set to create a field shape to provide a broad and uniform modulation field such as may be useful to prime targeted neural tissue with sub-perception modulation. Some examples are configured to determine a modulation parameter set to create a field shape to reduce or minimize modulation of non-targeted tissue (e.g., dorsal column tissue). Various examples disclosed herein are directed to shaping the modulation field to enhance modulation of some neural structures and diminish modulation at other neural structures. The modulation field may be shaped by using multiple independent current control (MICC) or multiple independent voltage control to guide the estimate of current fractionalization among multiple electrodes and estimate a total amplitude that provide a desired strength. For example, the modulation field may be shaped to enhance the modulation of dorsal horn neural tissue and to minimize the modulation of dorsal column tissue. A benefit of MICC is that MICC accounts for various in electrode-tissue coupling efficiency and perception threshold at each individual contact, so that "hotspot" stimulation is eliminated.

The number of electrodes available combined with the ability to generate a variety of complex electrical pulses, presents a vast selection of available modulation parameter sets to the clinician or patient. For example, if the neurostimulation system to be programmed has sixteen electrodes, millions of modulation parameter value combinations may be available for programming into the neurostimulation system. Furthermore, some SCS systems have as many as thirty-two electrodes, which exponentially increases the number of modulation parameter value combinations available for programming.

Figure 3:
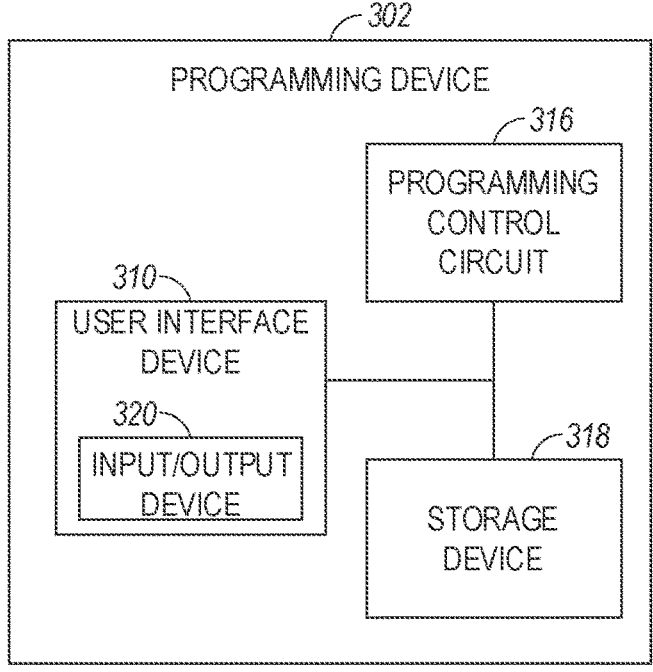
FIG. 3 illustrates, by way of example and not limitation, a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a user-interface device 310. Programming control circuit 316 generates the plurality of stimulation parameters that controls the delivery of the neurostimulation pulses according to the pattern of the neurostimulation pulses. The user-interface device 310 represents an embodiment to implement the user interface 110.

In various embodiments, the user-interface device 310 includes an input/output device 320 that is capable to receive user interaction and commands to load, modify, and implement neurostimulation programs and schedule delivery of the neurostimulation programs. In various embodiments, the input/output device 320 allows the user to create, establish, access, and implement respective parameter values of a neurostimulation program through graphical selection (e.g., in a graphical user interface output with the input/output device 320), or other graphical input/output relating to therapy objectives, efficacy of applied treatment, user feedback, and the like. In various examples, the user-interface device 310 can receive user input to initiate or control the implementation of the programs or program changes which are recommended, modified, selected, or loaded through use of an open or closed loop programming system, including those driven by freeform text analysis as discussed herein. In some examples, the user-interface device 310 can receive a user input including information about a personalized objective of neuromodulation treatment (e.g., SCS for pain management) or an intended manner of using the neuromodulation device by the patient. By way of example and not limitation, the personalized objective of neuromodulation treatment can include a desired physical state, such as an higher physical activity capacity, a quality sleep, a reduction of pain, or an elevated mood. The personalized intended neuromodulation device usage can include, for example, a desired device charging schedule or frequency, a desired power usage mode of the neuromodulation device, a desired amount of user interactions with the user-interface device, or a desired amount of time spent on therapy management, among others.

In various embodiments, the input/output device 320 allows the patient user to apply, change, modify, or discontinue certain building blocks of a program and a frequency at which a selected program is delivered. In various embodiments, the input/output device 320 can allow the patient user to save, retrieve, and modify programs (and program settings) loaded from a clinical encounter, managed from the patient feedback computing device, or stored in storage device 318 as templates. In various embodiments, the input/output device 320 and accompanying software on the user-interface device 310 allows newly created building blocks, program components, programs, and program modifications to be saved, stored, or otherwise persisted in storage device 318. Thus, it will be understood that the user-interface device 310 may allow many forms of device operation and control, even if closed loop programming is occurring. The analysis of freeform text, discussed herein, may be in addition to (or in place of) this user input and other forms of closed-loop or open-loop programming.

In one embodiment, the input/output device 320 includes a touchscreen. In various embodiments, the input/output device 320 includes any type of presentation device, such as interactive or non-interactive screens, and any type of user input device that allows the user to interact with a user interface to implement, remove, or schedule the programs. Thus, the input/output device 320 may include one or more of a touchscreen, keyboard, keypad, touchpad, trackball, joystick, and mouse. The logic of the user interface 110, the stimulation control circuit 214, and the programming control circuit 316, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller circuit or portions thereof, and a programmable logic circuit or a portion thereof.

Figure 4:
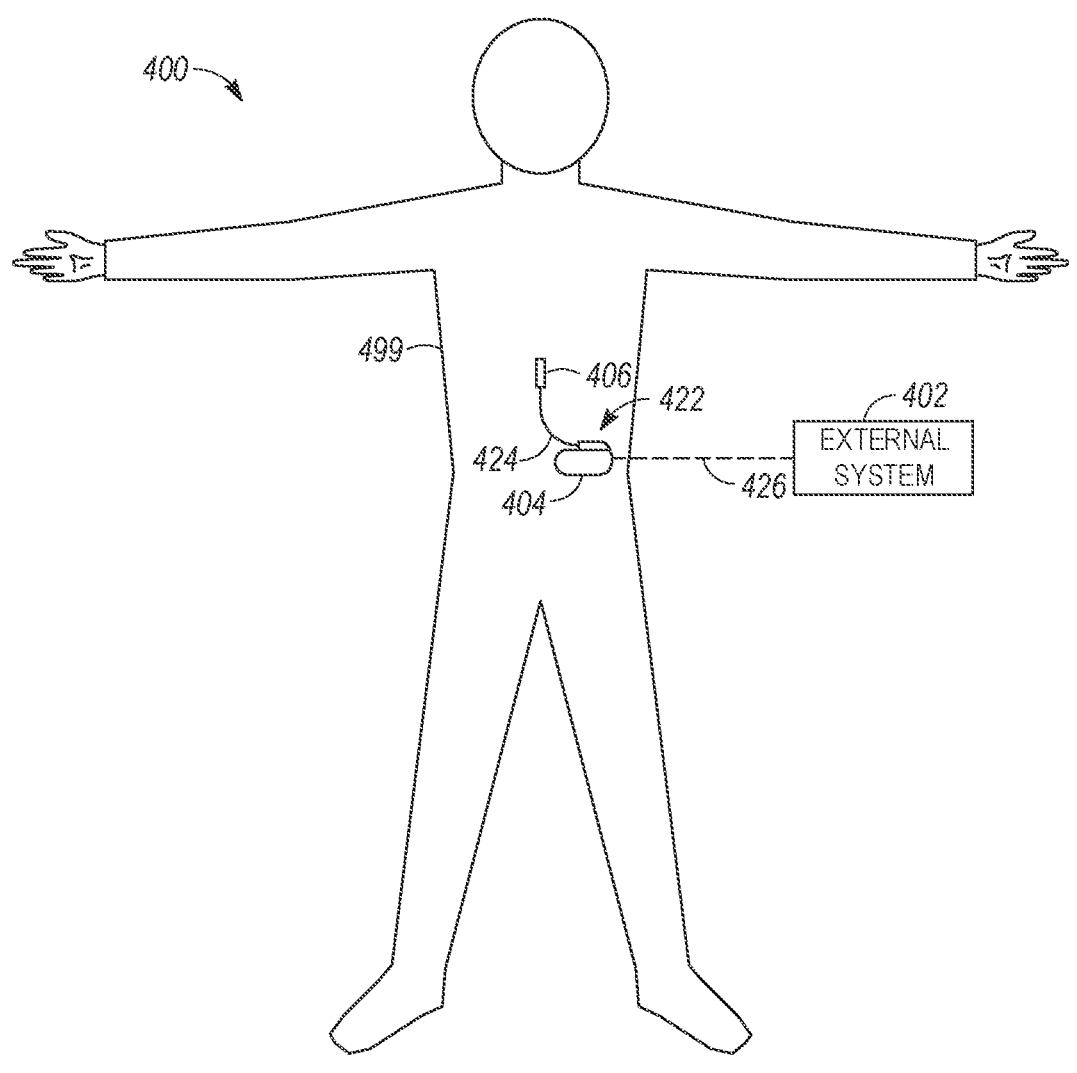
FIG. 4 illustrates, by way of example and not limitation, an implantable neurostimulation system and portions of an environment in which the system may be used.

FIG. 4 illustrates an implantable neurostimulation system 400 and portions of an environment in which system 400 may be used. System 400 includes an implantable system

422, an external system 402, and a telemetry link 426 providing for wireless communication between an implantable system 422 and an external system 402. Implantable system 422 is illustrated in FIG. 4 as being implanted in the patient's body 499. The system is illustrated for implantation near the spinal cord. However, the neuromodulation system may be configured to modulate other neural targets.

Implantable system 422 includes an implantable stimulator 404 (also referred to as an implantable pulse generator, or IPG), a lead system 424, and electrodes 406, which represent an embodiment of the stimulation device 204, the lead system 208, and the electrodes 206, respectively. The external system 402 represents an embodiment of the programming device 302.

In various embodiments, the external system 402 includes one or more external (non-implantable) devices each allowing the user and/or the patient to communicate with the implantable system 422. In some embodiments, the external system 402 includes a programming device intended for the user to initialize and adjust settings for the implantable stimulator 404 and a remote control device intended for use by the patient. For example, the remote control device may allow the patient to turn the implantable stimulator 404 on and off and/or adjust certain patient-programmable parameters of the plurality of stimulation parameters. The remote control device may also provide a mechanism to receive and process feedback on the operation of the implantable neuromodulation system. Feedback may include metrics or an efficacy indication reflecting perceived pain, effectiveness of therapies, or other aspects of patient comfort or condition. Such feedback may be automatically detected from a patient's physiological state, collected from other sensors or devices (not shown), or manually obtained from user input entered in a user interface (such as with the user input scenarios discussed below). Such feedback and other information may comprise the device data evaluated as part of association and matching with freeform text input.

As used herein, the terms "neurostimulator," "stimulator," "neurostimulation," and "stimulation" generally refer to the delivery of electrical energy that affects the neuronal activity of neural tissue, which may be excitatory or inhibitory; for example by initiating an action potential, inhibiting or blocking the propagation of action potentials, affecting changes in neurotransmitter/neuromodulator release or uptake, and inducing changes in neuro-plasticity or neurogenesis of tissue. It will be understood that other clinical effects and physiological mechanisms may also be provided through use of such stimulation techniques.

FIG. 5 illustrates an embodiment of the implantable stimulator 404 and the one or more leads 424 of an implantable neurostimulation system, such as the implantable system 422. The implantable stimulator 404 may include a sensing circuit 530 used for an optional sensing capability, stimulation output circuit 212, a stimulation control circuit 514, an implant storage device 532, an implant telemetry circuit 534, and a power source 536. The sensing circuit 530, when included and needed, senses one or more physiological signals for purposes of patient monitoring and/or feedback control of the neurostimulation, including in the closed loop programming processes discussed herein. Examples of the one or more physiological signals includes neural and other signals each indicative of a condition of the patient that is treated by the neurostimulation and/or a response of the patient to the delivery of the neurostimulation.

The stimulation output circuit 212 is electrically connected to electrodes 406 through the one or more leads 424, and delivers each of the neurostimulation pulses through a set of electrodes selected from the electrodes 406. The stimulation output circuit 212 can implement, for example, the generating and delivery of a customized neurostimulation waveform (e.g., implemented from a parameter of a program selected with the closed-loop programming system) to an anatomical target of a patient.

The stimulation control circuit 514 represents an embodiment of the stimulation control circuit 214 and controls the delivery of the neurostimulation pulses using the plurality of stimulation parameters specifying the pattern of the neurostimulation pulses. In one embodiment, the stimulation control circuit 514 controls the delivery of the neurostimulation pulses using the one or more sensed physiological signals and processed input from patient feedback interfaces. The implant telemetry circuit 534 provides the implantable stimulator 404 with wireless communication with another device such as a device of the external system 402, including receiving values of the plurality of stimulation parameters from the external system 402. The implant storage device 532 stores values of the plurality of stimulation parameters, including parameters from one or more programs which are activated, de-activated, or modified using the approaches discussed herein.

The power source 536 provides the implantable stimulator 404 with energy for its operation. In one embodiment, the power source 536 includes a battery. In one embodiment, the power source 536 includes a rechargeable battery and a battery charging circuit for charging the rechargeable battery. The implant telemetry circuit 534 may also function as a power receiver that receives power transmitted from external system 402 through an inductive couple.

In various embodiments, the sensing circuit 530, the stimulation output circuit 212, the stimulation control circuit 514, the implant telemetry circuit 534, the implant storage device 532, and the power source 536 are encapsulated in a hermetically sealed implantable housing. In various embodiments, the lead(s) 424 are implanted such that the electrodes 406 are placed on and/or around one or more targets to which the neurostimulation pulses are to be delivered, while the implantable stimulator 404 is subcutaneously implanted and connected to the lead(s) 424 at the time of implantation.

FIG. 6 illustrates an embodiment of a programming system 602 used as part of an implantable neurostimulation system, such as the external system 402, with the programming system 602 configured to send and receive device data (e.g., commands, parameters, program selections, information). FIG. 6 also illustrates an embodiment of a data analysis computing system 650, communicatively coupled to the programming system 602, with the data analysis computing system 650 used to perform data analysis on freeform text and device data in connection with neuromodulation treatment by the implantable neurostimulation system.

The programming system 602 represents an embodiment of the programming device 302, and includes an external telemetry circuit 640, an external storage device 616, a programming control circuit 620, a user-interface device 610, a controller circuit 630, and an external communication device 618, to effect programming of a connected neuromodulation device. The operation of the neurostimulation parameter selection circuit 622 enables selection, modification, and implementation of a particular set of parameters or settings for neurostimulation programming.

The external telemetry circuit 640 provides the closed loop programming system 602 with wireless communication to and from another controllable device such as the implantable stimulator 404 via the telemetry link 426, including transmitting one or a plurality of stimulation parameters (including selected, identified, or modified stimulation parameters of a selected program) to the implantable stimulator 404. In one embodiment, the external telemetry circuit 640 also transmits power to the implantable stimulator 404 through inductive coupling.

The external communication device 618 may provide a mechanism to conduct communications with a programming information source, such as a data service, program modeling system, to receive program information, settings and values, models, functionality controls, or the like, via an external communication link (not shown). In a specific example, the external communication device 618 communicates with the data analysis computing system 650 to obtain commands or instructions in connection with parameters or settings that are selected, modified, or implemented based on freeform text analysis from the data analysis computing system 650. The external communication device 618 may communicate using any number of wired or wireless communication mechanisms described in this document, including but not limited to IEEE 802.11 (Wi-Fi), Bluetooth, Infrared, and like standardized and proprietary wireless communications implementations. Although the external telemetry circuit 640 and the external communication device 618 are depicted as separate components within the closed-loop programming system 602, the functionality of both of these components may be integrated into a single communication chipset, circuitry, or device.

The external storage device 616 stores a plurality of existing neurostimulation waveforms, including definable waveforms for use as a portion of the pattern of the neurostimulation pulses, settings and setting values, other portions of a program, and related treatment efficacy indication values. In various embodiments, each waveform of the plurality of individually definable waveforms includes one or more pulses of the neurostimulation pulses, and may include one or more other waveforms of the plurality of individually definable waveforms. Examples of such waveforms include pulses, pulse blocks, pulse trains, and train groupings, and programs. The existing waveforms stored in the external storage device 616 can be definable at least in part by one or more parameters including, but not limited to the following: amplitude, pulse width, frequency, duration (s), electrode configurations, total charge injected per unit time, cycling (e.g., on/off time), waveform shapes, spatial locations of waveform shapes, pulse shapes, number of phases, phase order, interphase time, charge balance, and ramping.

The external storage device 616 may also store a plurality of individually definable fields that may be implemented as part of a program. Each waveform of the plurality of individually definable waveforms is associated with one or more fields of the plurality of individually definable fields. Each field of the plurality of individually definable fields is defined by one or more electrodes of the plurality of electrodes through which a pulse of the neurostimulation pulses is delivered and a current distribution of the pulse over the one or more electrodes. A variety of settings in a program may be correlated to the control of these waveforms and definable fields.

The programming control circuit 620 represents an embodiment of a programming control circuit 316 and may translate or generate the specific stimulation parameters or changes which are to be transmitted to the implantable stimulator 404, based on the results of the neurostimulation parameter selection circuit 622. The pattern may be defined using one or more waveforms selected from the plurality of individually definable waveforms (e.g., defined by a program) stored in an external storage device 616. In various embodiments, the programming control circuit 620 checks values of the plurality of stimulation parameters against safety rules to limit these values within constraints of the safety rules. In one embodiment, the safety rules are heuristic rules.

The user-interface device 610 represents an embodiment of the user-interface device 310 and allows the user (including a patient or clinician) to provide input relevant to therapy objectives, such as to switch programs or change operational use of the programs. The user-interface device 610 includes a display screen 612, a user input device 614, and may implement or couple to the parameter selection circuit 622, or data provided from the data analysis computing system 650. The display screen 612 may include any type of interactive or non-interactive screens, and the user input device 614 may include any type of user input devices that supports the various functions discussed in this document, such as a touchscreen, keyboard, keypad, touchpad, trackball, joystick, and mouse. Similar to the user-interface device 310 as discussed above, the user-interface device 610 can allow the user to provide user input including information about a personalized objective of neuromodulation treatment (e.g., SCS for pain management) or an intended manner of using the neuromodulation device. Such input information may be processed by the data analysis computing system 650 to generate a personalized treatment and device usage goal for the patient. The user-interface device 610 may also allow the user to perform other functions where user interface input is suitable (e.g., to select, modify, enable, disable, activate, schedule, or otherwise define a program, sets of programs, provide feedback or input values, or perform other monitoring and programming tasks). Although not shown, the user-interface device 610 may also generate a visualization of such characteristics of device implementation or programming, and receive and implement commands to implement or revert the program and the neurostimulator operational values (including a status of implementation for such operational values). These commands and visualization may be performed in a review and guidance mode, status mode, or in a real-time programming mode.

The controller circuit 630 can be a microprocessor that communicates with the external telemetry circuit 640, the external communication device 618, the external storage device 616, the programming control circuit 620, the parameter selection circuit, and the user-interface device 610, via a bidirectional data bus. The controller circuit 630 can be implemented by other types of logic circuitry (e.g., discrete components or programmable logic arrays) using a state machine type of design. As used in this disclosure, the term "circuitry" should be taken to refer to discrete logic circuitry, firmware, or to the programming of a microprocessor.

The data analysis computing system 650 is configured to operate treatment action circuitry 660, which may produce or initiate certain actions on the basis of device data (received and processed by device data processing circuit 652) and freeform input text or voices (received and processed by text processing circuit 654). The treatment action circuitry 660 may identify one or more actions related to the neuromodulation treatment, and provide outputs to a patient or a clinician using patient output circuitry 662 or clinician output circuitry 664, respectively. Such outputs and actions provided by the outputs are based on the evaluation and detection of particular patient states and device states from freeform text and associated device data, discussed in more detail below.

The data analysis computing system 650 also is depicted as including a storage device 656 to store or persist data related to the device data, freeform text input, patient or clinician output, and related settings, logic, or algorithms. Other hardware features of the data analysis computing system 650 are not depicted for simplicity, but are suggested from functional capabilities and operations in the following figures.

As will be understood, patients who are experiencing chronic pain are often willing to provide detailed information regarding their current medical state, treatment or physical objectives using freeform text either voluntarily or prompted with questions. Freeform text in the form of a narrative, explanatory statement, or interjection is easy for patients to produce, and can provide many details regarding a patient's actions, physiological and physiological state, prior historical events, treatment and physical objectives, desired operation mode or a habit of usage of the neuromodulation device, and can reflect both objective and subjective results of neuromodulation treatment. Freeform text, however, can be time-consuming or difficult for physicians and clinicians to interpret, especially when patient feedback may be contradictory (e.g., "I felt good in the morning but was unable to do any activity") or is incomplete without additional context (e.g., "I was unable to get out of bed."). Additionally or alternatively, text or voice expressions about patient personalized treatment or QoL goals, such as "I want be more active" or "I want to have better sleep," are vague and lack specificity, which may lead to inaccurate or inconsistent goal-tracking performance. Systems and methods described in this document in accordance to various embodiments can more efficiently interpret patient text or voice input, produce quantifiable goal metrics and determine patient state based on the interpretation, produce useful outcomes for diagnosis, treatment, and remediation relevant to neuromodulation device operation, and conveniently and effectively track patient progress toward a preset treatment and device usage goal.

Figure 7:
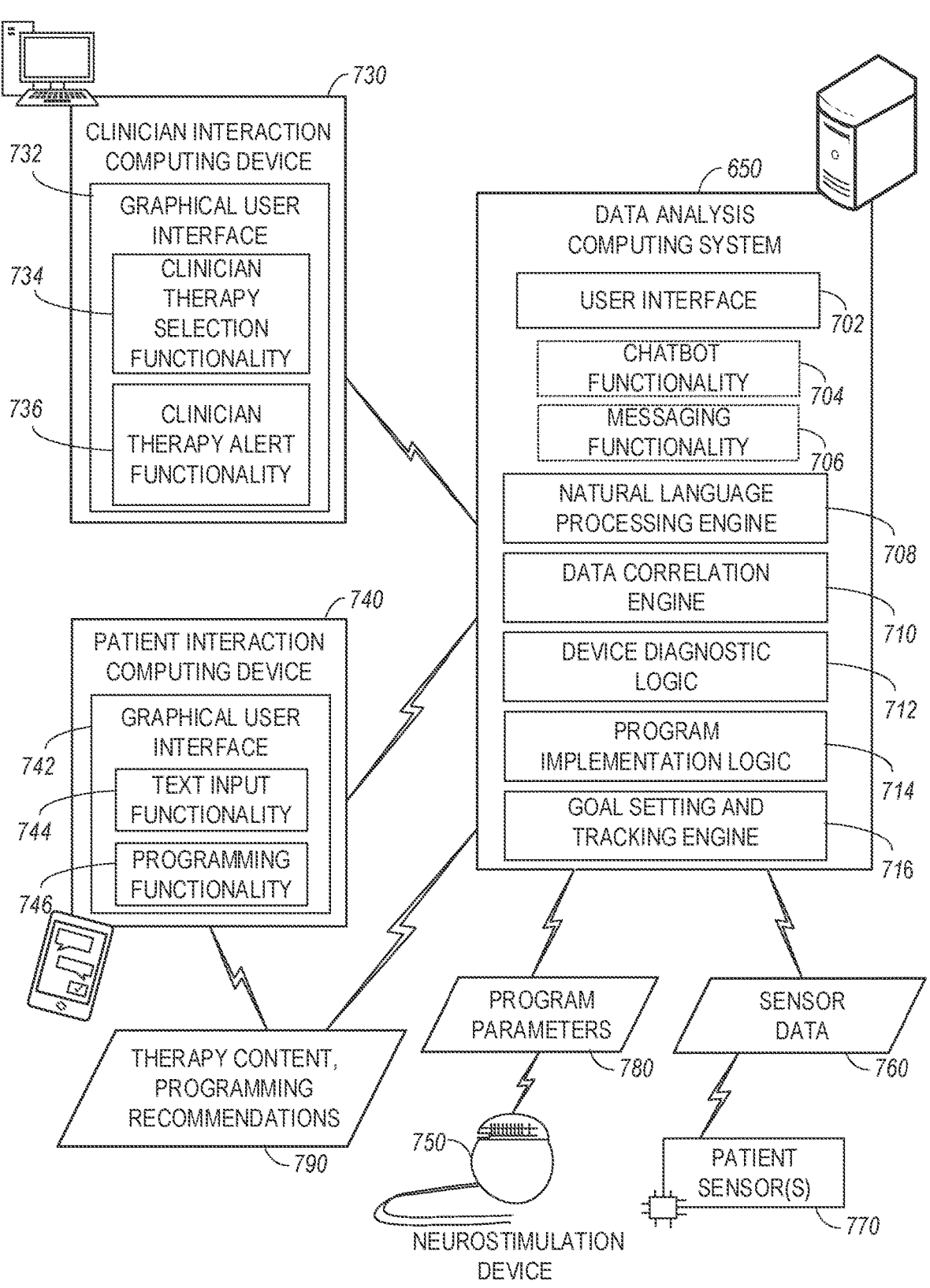
FIG. 7 illustrates, by way of example and not limitation, data interactions among a data analysis computing system and clinician and patient interaction computing devices, for operation or monitoring of a neuromodulation device, including setting and tracking a personalized treatment and device usage goal, based on text input analysis.

FIG. 7 illustrates, by way of example, an embodiment of data interactions among the data analysis computing system 650 and one or more of a clinician interaction computing devices 730 or a patient interaction computing devices 740, for operation of a neuromodulation device 750, including setting and tracking a personalized treatment and device usage goal, based on freeform text analysis of user input. At a high level, the data analysis computing system 650 identifies operations related to the neuromodulation treatment based on the analysis of input text, such as diagnostic actions, alerts, content or programming recommendations, or programming actions. Such programming actions (and, operational actions based on programming recommendations) may be implemented on the neuromodulation device 750 (e.g., using the programming techniques discussed above). The data analysis computing system 650 identifies and initiates these actions through the execution of one or more data analysis engines, such as a natural language processing (NLP) engine 708 which parses freeform text input and determines therefrom a state of a patient or a personalized treatment and device usage goal, and data correlation engine 710 which determines a state of treatment from historical or current operation of the neuromodulation device 750. In some examples, the determined state of treatment may be based on correlating the historical use of a neurostimulation program or set of parameters with the current state of a patient (e.g., identifying that a pain condition became worse after beginning use of a particular program at a previous point in time).

Specifically, the data analysis computing system 650 operates the NLP engine 708 to analyze text or voice input originating from a patient that is relevant to neuromodulation treatment. As described above with reference to FIGS. 3 and 6, the text or voice input can include information about a personalized objective of neuromodulation treatment or an intended manner of using the neuromodulation device by the patient, which may be used to set a personalized treatment and device usage goal. In some examples, the text or voice input can represent patient feedback on the neuromodulation treatment or execution of the personalized treatment and device usage goal. The text or voice form of feedback may be processed using various techniques including text parsing, linguistic analysis, topic modeling, etc. to determine the progress toward the personalized treatment and device usage goal. The text or voice input may be received via a user interface 702 of the data analysis computing system 650, such as provided from chatbot functionality 704 or messaging functionality 706. The text or voice input also may be provided from a patient interaction computing device 740, or other third party devices and platforms not depicted.

The data analysis computing system 650 also operates a data correlation engine 710 to correlate (e.g., identify, match, associate) device state data and patient state data, a device diagnostic logic 712 to evaluate operational or conditions from the neuromodulation device 750, a program implementation logic 714 to effect changes in programming to the neuromodulation device 750, and a goal setting and tracking engine 716 to generate a personalized treatment and device usage goal for the patient and to track patient progress toward the personalized treatment and device usage goal. In an example, the program implementation logic 714 enables control, modification, selection, or specification of neurostimulation programming parameters, in an automatic, suggested, or manual fashion. Additional detail regarding programming of the device 750 is provided with reference to FIG. 10, and it will be understood that other embodiments of program modeling, selection, recommendation, and implementation may be provided via programming devices, data services, or information services which are not depicted.

In an example, the NLP engine 708 applies one or more approaches for analysis of text. One such approach may include topic modeling, which is an unsupervised machine learning approach that can be used to discover and identify topical concepts from a corpus of text. For example, a NLP model which uses topic modeling may be trained on related text topics, and then deployed to identify if a text comment is on-topic to the use of a neurostimulation or not (e.g., to determine relevancy of the text to one or more topics). Topic modeling is a machine learning approach to identify word and phrase patterns within textual input (e.g., a series of documents), and automatically cluster word groupings and related expressions that best represent the set. Topic modeling may also be used to identify different troubleshooting areas relevant to operation of a neuromodulation device such as charging, remote controls, etc. In some examples, topic modeling may be used to identify a goal type from the text or voice input about a personalized objective of neuromodulation treatment, such as a sleep goal, a mobility goal, a pain reduction goal, an emotion goal of emotional wellness, etc. The identified goal type may be used by the goal setting and tracking engine 716 to determine a performance metric that quantifies a personalized treatment or device usage goal for the patient.

The goal setting and tracking engine 716 can generate a personalized treatment and device usage goal, and track progress toward the personalized treatment and device usage goal using processed data or output from one or more of the NLP engine 708, the data correlation engine 710, or the device diagnostic logic 712. For example, text or voice input from the patient about a personalized objective of neuromodulation treatment or an intended manner of using the neuromodulation device by the patient can be processed by the NLP engine 708, and the goal setting and tracking engine 716 can generate a personalized treatment and device usage goal based at least on the processed user input. The goal setting and tracking engine 716 can track the patient's progress toward the personalized treatment and device usage goal using patient feedback (e.g., in text or voice form) on the neuromodulation treatment or an execution of the personalized treatment and device usage goal processed and interpreted by the NLP engine 708, physiological or functional data collected from the patient by the neuromodulation device 750 or one or more patient sensors 770, the correlated data between the device data and the patient feedback produced by the data correlation engine 710, or the device diagnostic data produced by the device diagnostic logic 712. Examples of the goal setting and tracking engine and its uses in generating and tracking different types of treatment and device usage goals are discussed below with reference to FIGS. 8-10.

In an example, the patient interaction computing device 740 is a computing device (e.g., a laptop computer, tablet, smartphone) or other form of user-interactive device which receives and provides interaction with a patient using a graphical user interface 742, text input functionality 744, and programming functionality 746. For instance, the text input functionality 744 may receive freeform text from a patient via questionnaires, surveys, messages, or other textual inputs. Such inputs may provide text related to pain or satisfaction, which can be used to identify a psychological or physiological state of the patient, neuromodulation treatment results, or related conditions. Although not depicted, other forms of non-text input functionality may also be provided.

The patient interaction computing device 740 is also depicted as including the programming functionality 746, to provide one or more outputs in the graphical user interface related to programming control or implementation. The programming functionality 746 specifically may provide the patient with therapy content and programming recommendations 790 generated by the data analysis computing system 650. Other form factors and interfaces such as audio interfaces and text interfaces may also be substituted for or augmented with the graphical user interface 742.

The clinician interaction computing device 730 may include a graphical user interface 732, which implements clinician therapy selection functionality 734 and clinician therapy alert functionality 736, offering similar capabilities to the graphical user interface 742 for the patient, but adapted for use by a clinician (e.g., to provide enhanced functionality or features for physician control). Although not depicted, the therapy content and programming recommendations 790 and enhanced information provided for clinicians can also be presented via the graphical user interface 732.

In an example, the data analysis computing system 650 generates, selects, or communicates therapy content and programming recommendations 790 to the patient interaction computing device 740 or the clinician interaction computing device 730. Such content and recommendations 790 are provided based on aspects of a correlated patient and device state, from a patient state detected from free text processing. The therapy content and programming recommendations 790 may include a recommendation or identification of the type of therapies to apply, instructions, recommendations, or feedback (including clinician recommendations, behavioral modifications, etc., selected for the patient). The therapy content and recommendations 790 also may provide relevant information based on the sensor data 760 or other neurostimulation state monitoring performed on the patient.

The data analysis computing system 650 may utilize sensor data 760 from one or more patient sensors 770 (e.g., wearables, sleep trackers, motion tracker, implantable devices, etc.) among one or more internal or external devices. The sensor data 760 may be used in addition to the program parameters 780, to determine a customized and current state of the patient condition or neuromodulation treatment results. In various examples, the neuromodulation device 750 includes sensors which contribute to the sensor data 760 evaluated by the data analysis computing system 650.

In an example, the patient sensors 770 are physiological or biopsychosocial sensors that collect data relevant to physical, biopsychosocial (e.g., stress and/or mood biomarkers), or physiological factors relevant to a state of the patient. Examples of such sensors might include a sleep sensor to sense the patient's sleep state (e.g., for detecting lack of sleep), a respiration sensor to measure patient breathing rate or capacity, a motion or activity sensor to identify an amount, type, intensity, or duration of movement or physical activities, a heart rate sensor to sense the patient's heart rate, a blood pressure sensor to sense the patient's blood pressure, an electrodermal activity (EDA) sensor to sense the patient's EDA (e.g., galvanic skin response), a facial recognition sensor to sense the patient's facial expression, a voice sensor (e.g., microphone) to sense the patient's voice, and/or an electrochemical sensor to sense stress biomarkers from the patient's body fluids (e.g., enzymes and/or ions, such as lactate or cortisol from saliva or sweat). Other types or form factors of sensor devices may also be utilized.

The following examples focus on various types of user interfaces and interactions which directly receive textual input from a patient. It will be understood that the text processing performed by the present approaches may occur on a variety of text input and sources of text content. Such text content may include the results from voice-to-text converted from voice phone or online calls with a medical device representative or a patient care entity. Further, it will be understood that relevant text data may be provided from voice, text, or multi-modal input from multiple channels (e.g., SMS text messages, an email, an app, a web site, a chatbot, a virtual universe meeting, etc.). Moreover, such text data may be provided from the conversion of voice-to-text from in-app voice recordings, voice chats, voicemails, or voice interactions with virtual assistants or agents (e.g., Amazon® Alexa, Google® Assistant, Apple® Siri, etc.). Analysis may also be performed on voice recordings directly to obtain relevant characteristics, such as to identify the vocal tone of the statement (e.g., analyzing the auditory signal itself to identify physiological or psychological characteristics of the patient such as calmness, irritation, sadness, etc.).

Figure 8A:
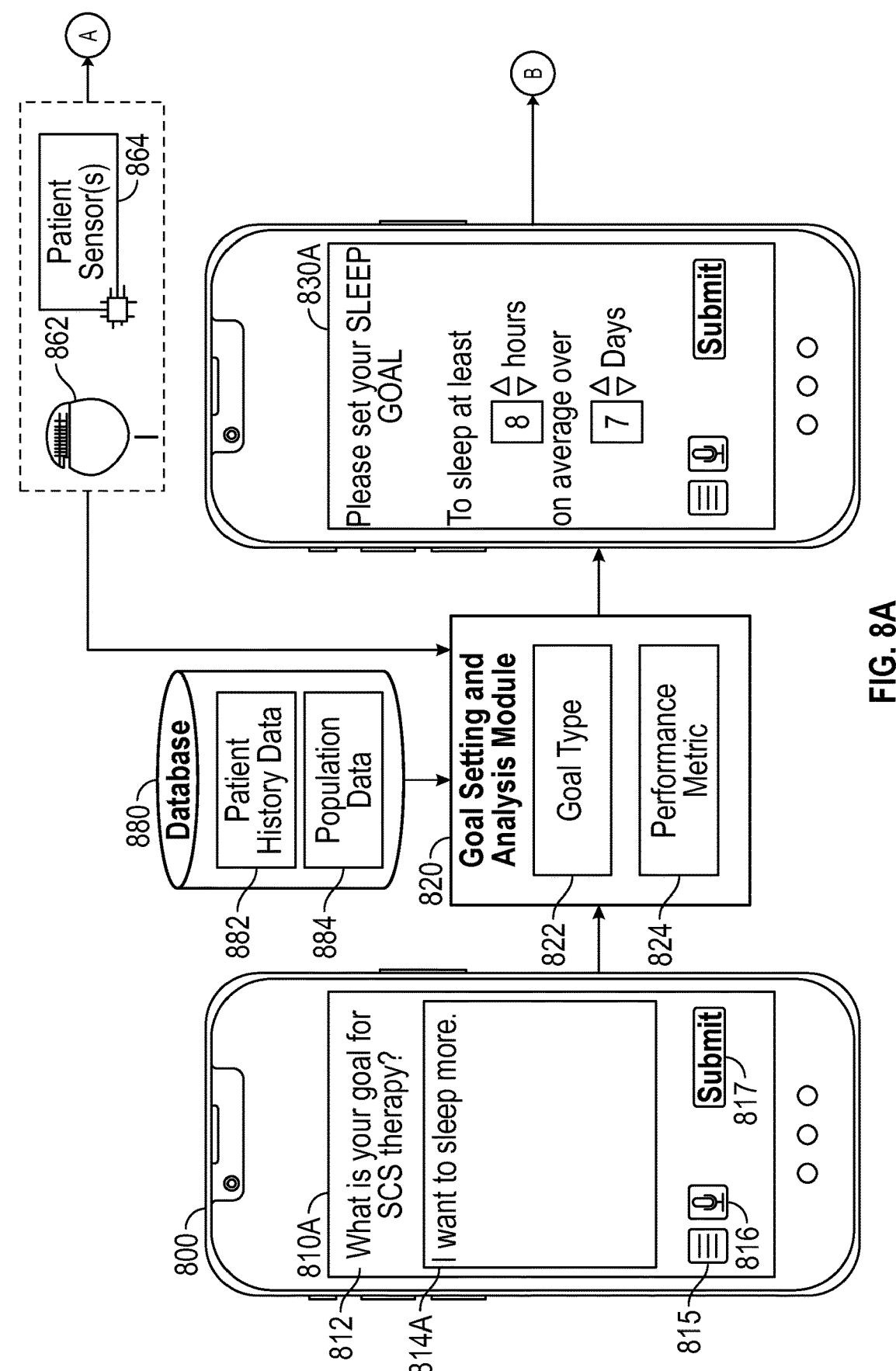
FIGS. 8A-8C illustrate, by way of example and not limitation, variations of user interfaces for receiving user input about an objective of neuromodulation treatment or about an intended manner of using the neuromodulation
Figure 8A:
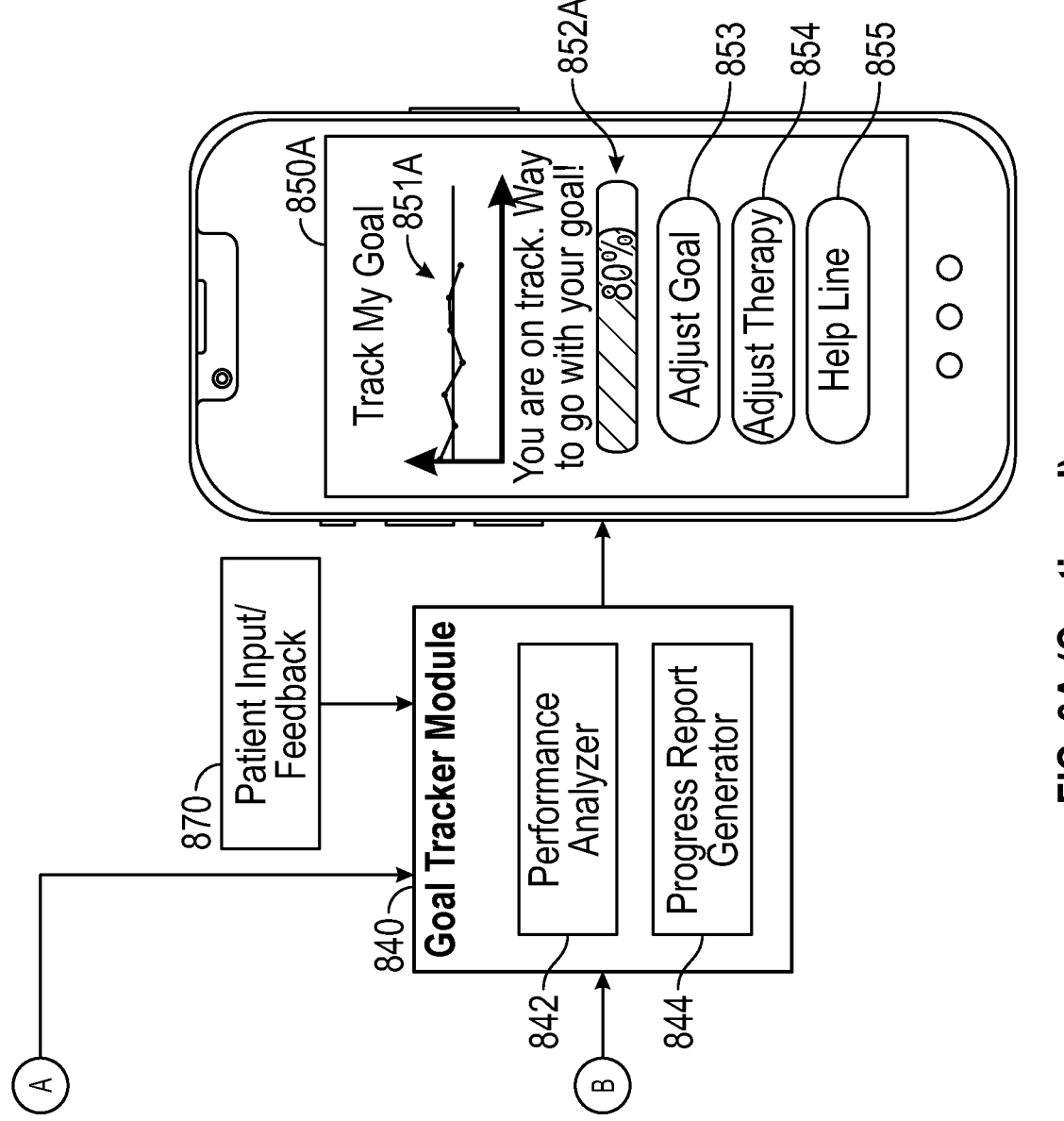
Figure 8B:
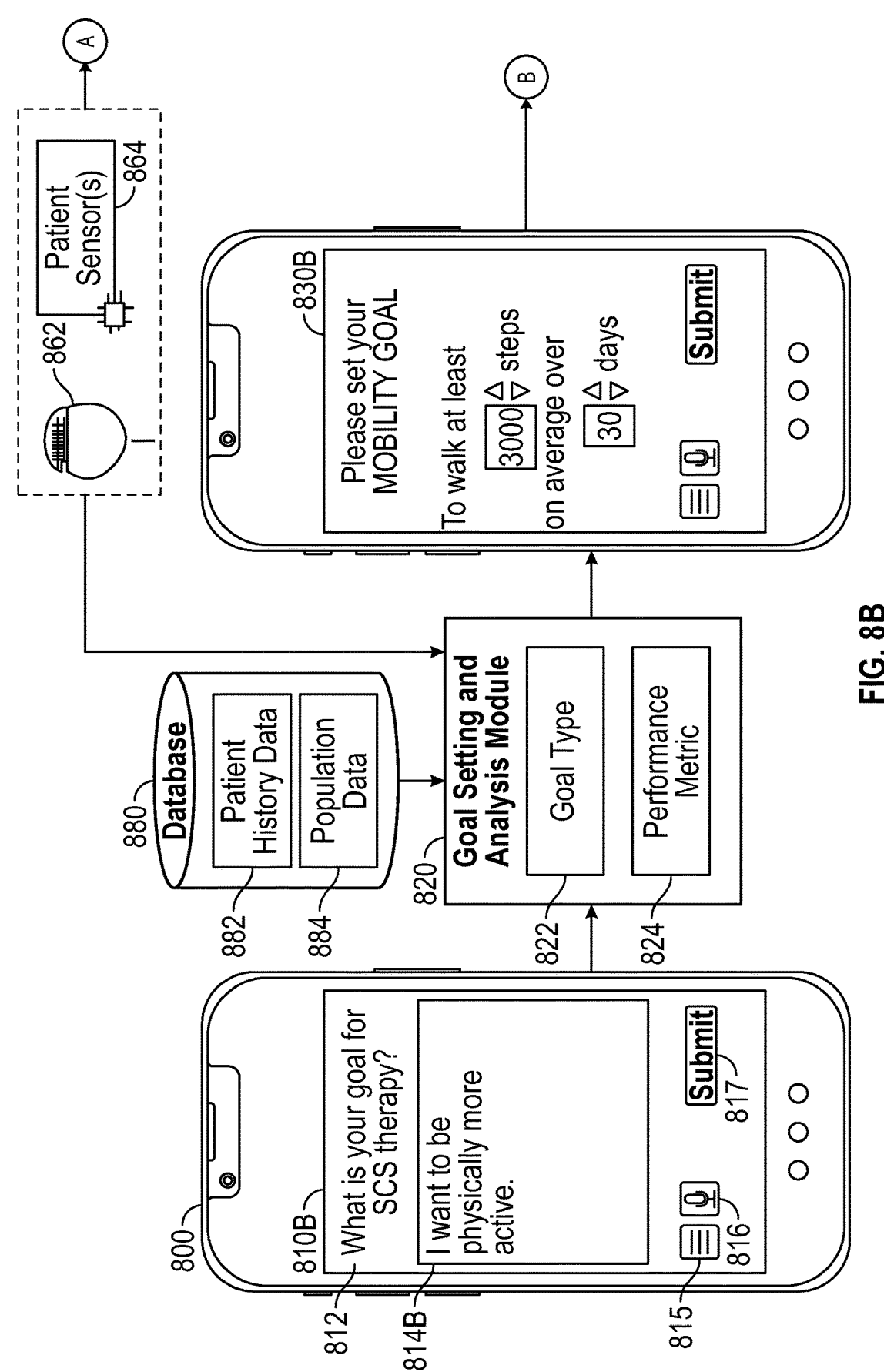
Figure 8B:
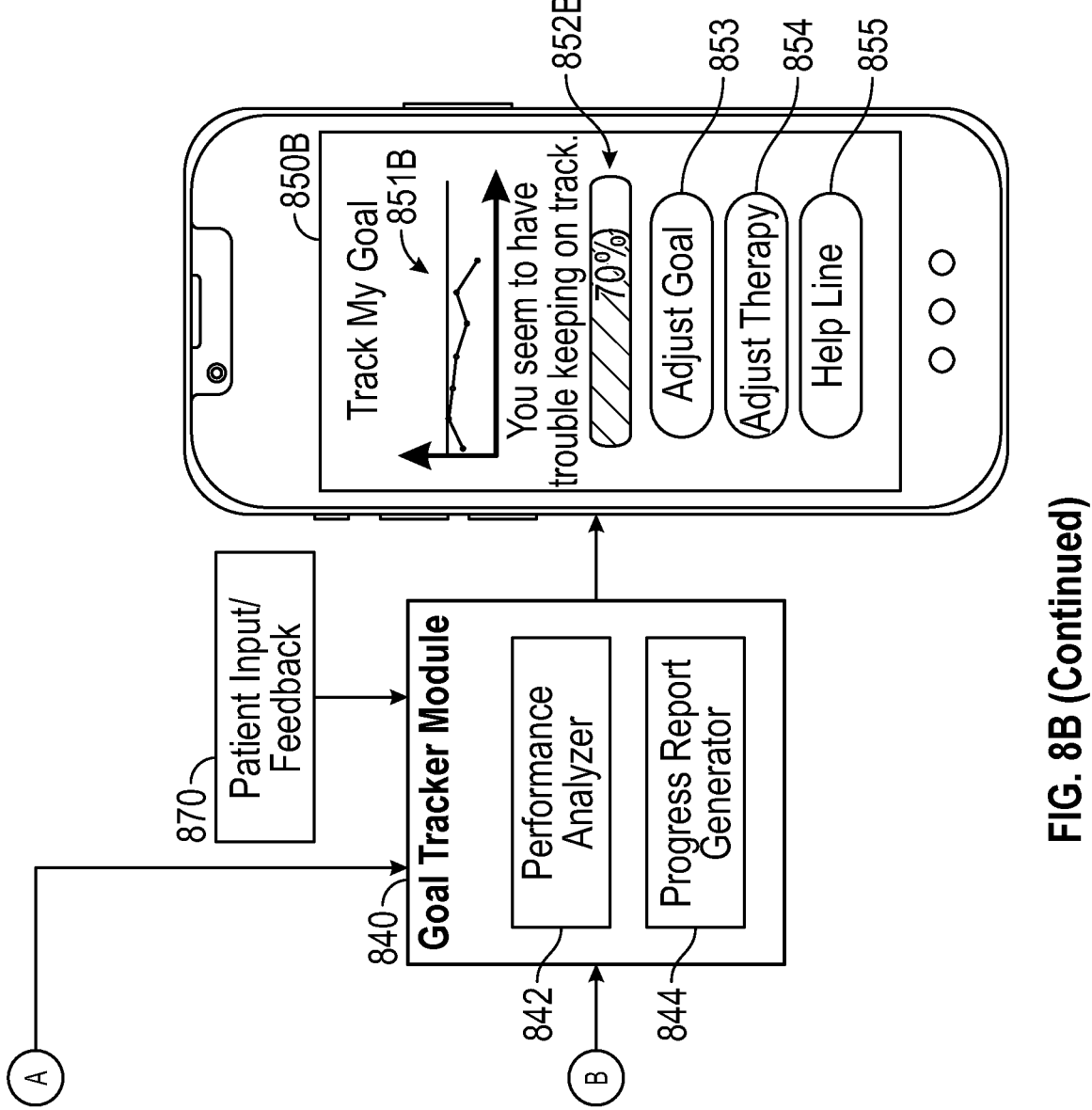
Figure 8C:
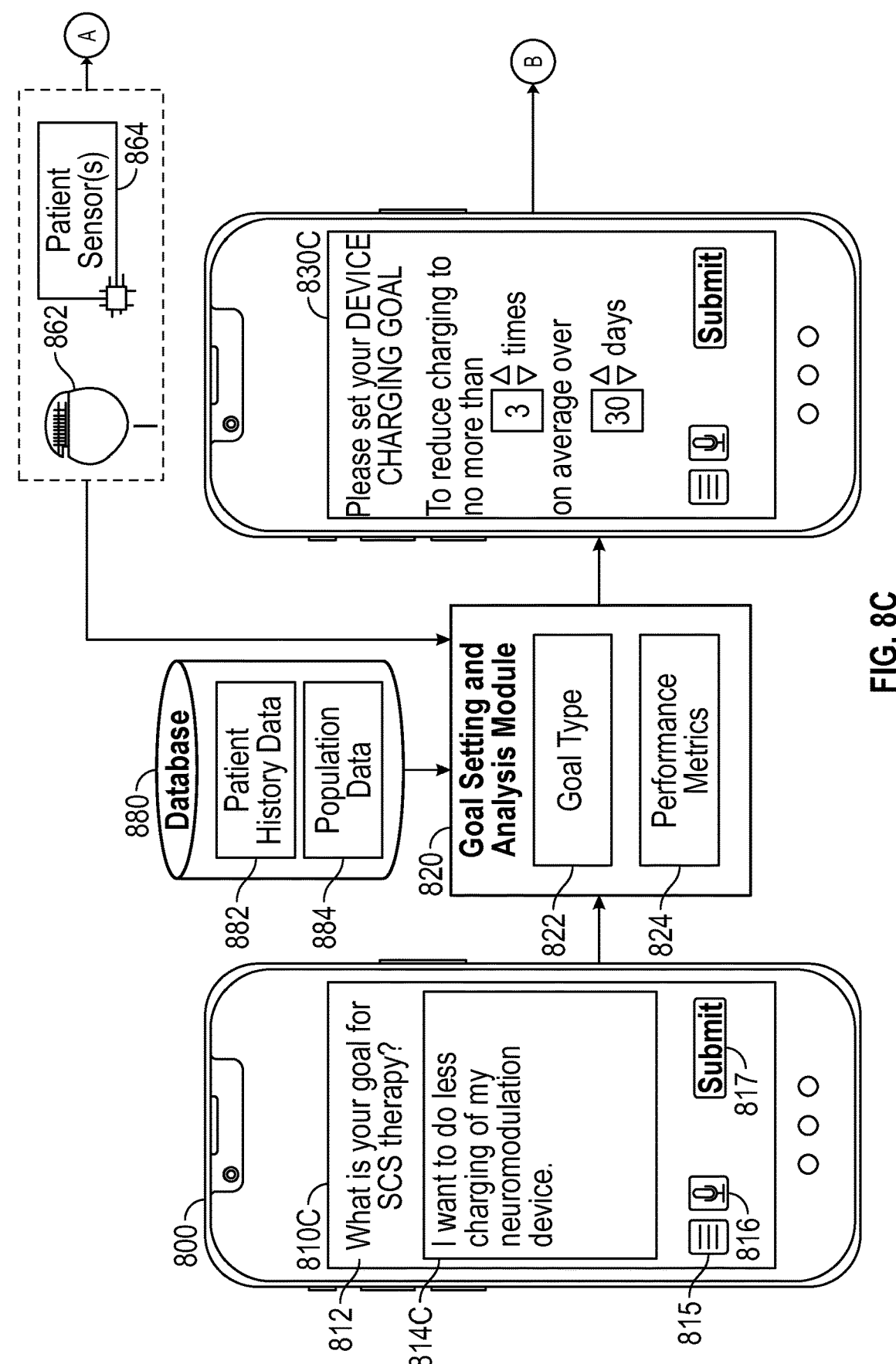
Figure 8C:
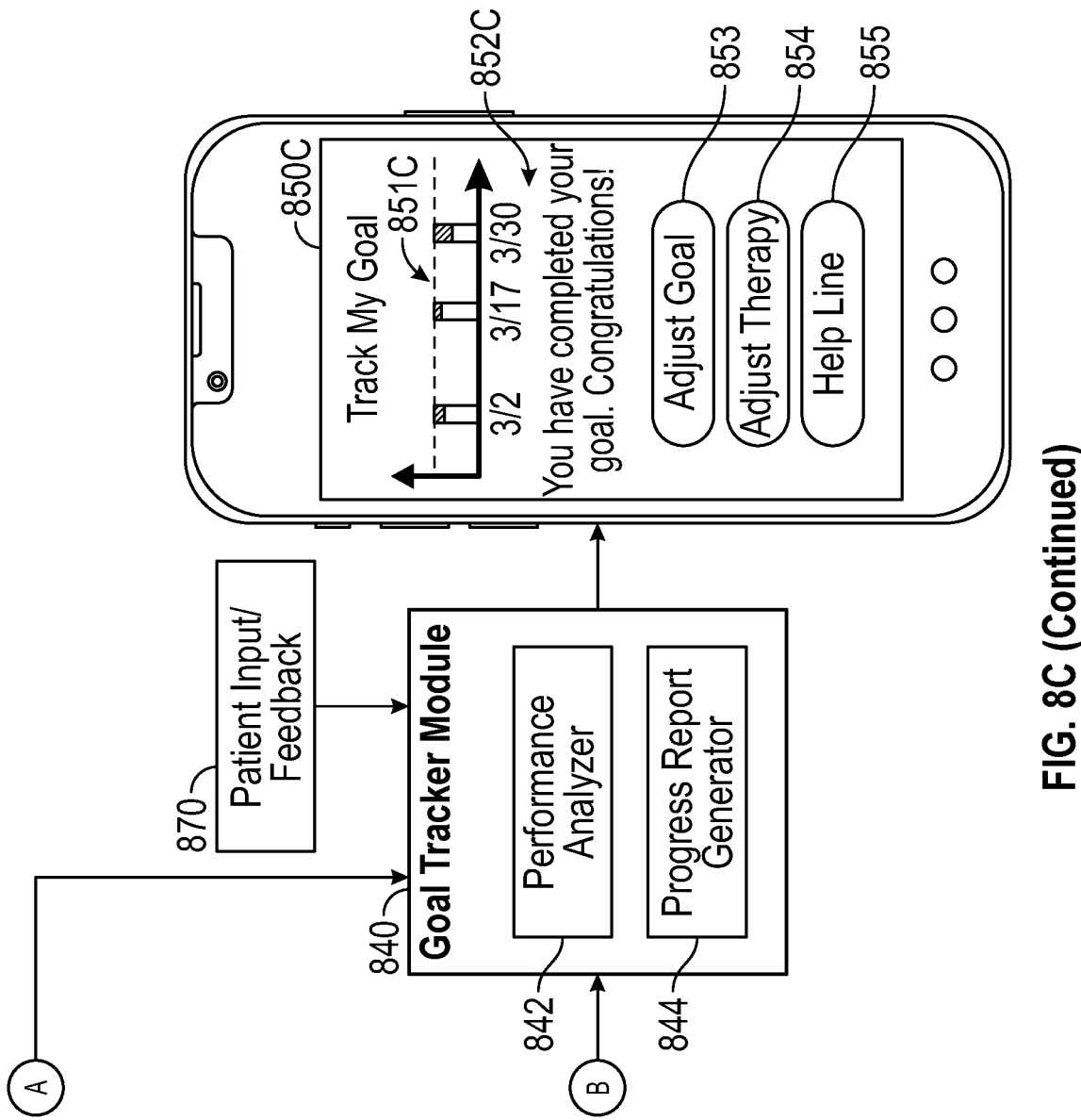

FIGS. 8A-8C illustrate, by way of example and not limitation, variations of user interfaces for receiving user input about an objective of neuromodulation treatment (as shown in FIGS. 8A and 8B) or about an intended manner of using the neuromodulation device (as shown in FIG. 8C), and various components of a computing system configured to generate and track a personalized treatment and device usage goal. In the illustrated examples, the user input is in a form of text or voice input. By way of example and not limitation, the user interfaces in FIGS. 8A-8C are depicted as operating on a mobile computing device 800 such as a smartphone. It will be understood that the user interfaces may alternatively be included in other types of mobile or stationary computing devices such as a laptop computer, a tablet, or a smart wearable device. The user interface can include one or more user interface (UI) controls, such as a keyboard control 815, a speech recognition control 816, or a submission control 817, among others not shown. Such UI controls allow a user (e.g., the patient) to provide text or voice input to set a personalized treatment and device usage goal, or to provide feedback to the treatment or execution of the set goal.

As illustrated in FIGS. 8A-8C, the user interface may display a question 812 about the treatment or device usage goal, and prompt the user to provide an answer in one or more forms such as freeform text or voice, optionally with one or more UI controls. The user input can include a neuromodulation treatment objective, such as symptom reduction (e.g., reduced pain), or an improved quality of life (QoL) metric, such as improved physical, personal autonomy, emotional, social, spiritual, or cognitive performances in patient daily life. Additionally or alternatively, the user input can include a device usage objective, such as an desired schedule or frequency for charging the neuromodulation device, a desired power usage mode for operating the neuromodulation device (e.g., a goal of limiting the time the neuromodulation device goes to hibernation mode), a desired amount of user interactions with the user-interface device, or a desired amount of time spent on therapy management. Specifically, FIG. 8A illustrates a user interface 810A being used to collect freeform text 814A related to a sleep goal "I want to sleep more." FIG. 8B illustrates a user interface 810B being used to collect freeform text 814B related to a mobility goal "I want to be physically more active." FIG. 8C illustrates a user interface 810C being used to collect freeform text 814C related to a device usage goal "I want to do less charging of my neuromodulation device."

The freeform text can be processed by a goal setting and analysis module 820, which can be included in or executed by the goal setting and tracking engine 716 as described above with reference to FIG. 7. The goal setting and analysis module 820 can process the freeform text input using a NLP algorithm, such as provided by the NLP engine 708. In an example, an NLP algorithm may be implemented with use of a rule-based sentiment analyzer. One such example of a sentiment analyzer is the VADER (Valence Aware Dictionary for sEntiment Reasoning) model, which uses a list of lexical features (e.g., words) that are positive or negative. This model is sensitive to both polarity (positive/negative) and intensity (strength) of emotion indicated within text. It will be understood that other models may be trained or turned with specific consideration of neuromodulation treatment and physiological conditions, and analysis or data values from multiple models may also be considered. Further, it will be understood that words can be masked or de-emphasized as part of the analysis.

The goal setting and analysis module 820 can process the freeform text 814A, 814B, or 814C to identify a goal type 822 using one of the methods such as keyword matching, topic modeling, linguistic analysis, etc. For example, a sleep goal type may be identified from the freeform text 814A, a mobility goal type may be identified from the freeform text 814B, and a device usage goal type may be identified from the freeform text 814C. The goal setting and analysis module 820 can further determine one or more performance metrics (also known as key performance indicators, or KPIs) 824 representing quantifiable measures to evaluate progress toward the identified goal type. In an example, the goal setting and analysis module 820 may use topic modeling to identify the goal type 822, and suggest the performance metrics 824 that are measurable to associate with the goal type 822. The specific, measurable performance metrics 824 can be used to set a personalized, quantifiable treatment goal for the patient. For example, for a sleep goal to "sleep more" as shown in FIG. 8A, the performance metrics may include a sleep duration (e.g., hours), a sleep quality indicator (e.g., sleep quality score between 0 and 5), or a sleep schedule (e.g., bedtime and wakeup time in a day or days such as weekdays and weekends), among others. For a mobility goal of being "physically more active" as shown in FIG. 8B, the performance metric may include daily amount (e.g., duration) or intensity of a particular type of activity, a workout schedule, a timespan for doing such activities, etc. For a device usage goal of "doing less device charging" shown in FIG. 8C, the performance metric may be represented by a number of times within a timeframe to charge the device, duration for each charge, etc.

In some examples, the goal setting and analysis module 820 may access a database 880, and receive therefrom patient history data 882 and/or population data 884 related to the identified goal type. The database 880 may be stored and maintained in the data analysis and computing system 650 or other storage devices. The patient history data 882 may include information about historical neuromodulation treatments and patient responses thereto or historical operations of the neuromodulation device. The population data 884 may include information about respective neuromodulation treatments and patient responses, or respective operations of the neuromodulation device, from a number of patients having similar medical conditions or similar demographics (collectively referred to as "similar patients") to the present patient. The goal setting and analysis module 820 may identify from the patient history data 882 the patient's past or habitual performance metrics as the baseline values for those metrics (e.g., a sleep duration of 6 hours per day), interpret the "sleep more" from the freeform text 814A using an NLP algorithm and determine accordingly a performance metric of daily sleep duration longer than the baseline value (e.g., at least 8 hours). Similarly, as shown in FIG. 8B, the goal setting and analysis module 820 may identify from the patient history data 882 the patient's past mobility metrics as the baseline values for those metrics (e.g., an average of 1000 steps daily, or daily mobility minutes such as one hour of running, 30 minutes of weight training, or 45 minutes of yoga), interpret the "physically more active" from the freeform text 814B using an NLP algorithm and determine accordingly a performance metric representing an exercise intensity of daily steps greater than the baseline value (e.g., 3000 steps). Likewise, as shown in FIG. 8C, the goal setting and analysis module 820 may identify from the patient history data 882 the patient's past or habitual device usage metrics as the baseline values for those metrics (e.g., charging device 5-8 times per month), interpret the "less charging of my device" from the freeform text 814C using an NLP algorithm and determine accordingly a performance metric representing a charge frequency no more than the baseline value (e.g., 3 times per month).

The goal setting and analysis module 820 may additionally or alternatively identify from the population data 884 performance metrics of the similar patients to the present patient, such as a population-based sleep metric (e.g., 8 hours sleep time in average across the patient population), a population-based physical activity metric (e.g., 3000-3500 steps per day across the patient population), or a population-based device usage metric (e.g., 3-4 times of charging the device per month across the patient population). The goal setting and analysis module 820 may interpret the freeform text 814A, 814B, or 814C and determine a personalized performance metric for the patient to substantially commensurate with the population-based performance metric (e.g., within a range of +/−10%).

The personalized, quantifiable treatment and device usage goal, including the goal type 822 and the performance metric 824, may be presented to a user (e.g., the patient) on a user interface, and the user may use one or more UI controls to accept, reject, or modify the personalized treatment and device usage goal. By way of examples, a graphical user interface 830A in FIG. 8A depicts an adjustable sleep goal, where the user may set or adjust the daily sleep duration (e.g., 8 hours) and the effective period for executing and tracking the sleep goal (e.g., 7 days). A graphical user interface 830B in FIG. 8B depicts an adjustable mobility goal, where the user may set or adjust daily steps (e.g., 3000 steps) and the effective period for executing and tracking the mobility goal (e.g., 30 days). A graphical user interface 830C in FIG. C depicts an adjustable device usage goal, where the user may set or adjust charging times (e.g., 3 times) and the effective period for executing and tracking the device usage goal (e.g., 30 days). Although the user interface 830A displays the quantifiable goals in texts with user adjustable performance metrics, it will be understood that the goal presentation and user adjustment may be achieved using other approaches.

In addition or alternative to the user input of personalized objective of neuromodulation treatment via the user interface 810A, in some examples, the goal setting and analysis module 820 may generate a personalized treatment and device usage goal, or a plurality of "candidate goals", based on information about patient state or condition even without the patient explicitly specifying his or her treatment objective or intended device usage pattern. The patient state or condition information may include physiological or functional information collected from the patient by the neuromodulation device 862, or other sensor devices 864 such as wearables, sleep trackers, motion tracker, among other devices. For example, if the physiological or functional information collected from a wearable tracker device (e.g., a sleep tracker app in a smartphone) indicates that the patient's sleep quality worsens (e.g., shorter durations or irregular schedules) or that the patient has become less physically active, the goal setting and analysis module 820 may automatically set a sleep goal similar to that shown in 830A or a mobility goal similar to the one shown in 830B. The patient state or condition information may additionally or alternatively include patient input or feedback 870 on his or her state or condition, QoL attributes, responses to neuromodulation treatment, among others. The patient input or feedback 870 may be provided as freeform text or voice messages on a user interface on the mobile computing device 800 or other user-interface devices such as a laptop computer, a tablet, or a smart wearable device. The patient input or feedback 870 can include answers to a questionnaire or an interactive questions and answers session (e.g., an automated chatbot session) on the user interface. The text content may indicate or relate to the state or the condition of a patient, such as with text content originating from conversations or feedback received from the patient. In specific examples, the text content originates from at least one of: text provided in a text chat session (e.g., transcript text) conducted between a chatbot and the patient; a voice chat session conducted between a virtual agent and the patient, with at least a portion of the voice chat session converted to text (e.g., a transcript of the chat session conversation); a text message session conducted between a text service and the patient (e.g., a transcript of one or more SMS text conversations); or an audio recording of a discussion conducted between the patient and a human agent, with at least a portion of the audio recording converted to text (e.g., a transcript of the audio recording); or a freeform text input provided by the patient (e.g., survey or question responses, narrations, etc.). The text or voice input or feedback can be processed using NLP algorithms or other text analysis methods as described above with reference to FIG. 7. In an example, an algorithm provided by the NLP engine can translate the patient freeform textual interactions to valence (polarity) scores. These polarity scores may represent a negative or positive sentiment (e.g., in a range from values −1 to +1), or an intensity of positive or negative sentiment, captured at or associated with a particular time. The polarity scores can be cross-referenced against device data (e.g., program usage, device on/off state, physiological state from a sensor, etc.), and the polarity of a particular text statement may be directly determined as a result of sentiment analysis performed using any number of NLP techniques. The polarity of a text statement and the resulting patient state may be used, for instance, to identify the most effective settings of a neurostimulation program, directly from patient feedback and responses collected over time. In another example, an NLP algorithm can translate the patient freeform textual interactions to specific device diagnostics to be initiated at specific time, such as to evaluate various aspects of device data from the neuromodulation device 862. This may include, checking current battery level, identifying a current program, identifying device impedance, verifying program settings, performing logging or evaluation of logging information, initiating troubleshooting procedures, and the like. U.S. Provisional Patent Application 63/287,828 provides a detailed disclosure of systems and methods for interpreting patient text or voice input, and producing useful outcomes for diagnosis, treatment, and remediation relevant to neuromodulation therapy and device operation, which are incorporated herein by reference in its entirety. If the patient freeform text or voice input indicates a worsened sleep quality or consistent physical inactivity, the goal setting and analysis module 820 may generate a sleep goal or a mobility goal, such as one similar to the goals shown in the user interfaces 830A or 830B, respectively.

In some examples, the goal setting and analysis module 820 may generate a plurality of selectable "candidate goals" based on topic modeling of the user input of the object of treatment or intended device usage (as shown in 814A, 814B, or 814C), patient history data 882 and/or population data 884, or patient state or condition as determined based on data from devices or sensors or various types or from patient input and feedback. For example, a plurality of sleep goals, mobility goals, or device usage goals most common to the similar patients can be presented on a user interface. The candidate goals may differ from each other by at least one performance metric value. Such candidate goals may be presented in a drop-down list, a list box, or other forms of UI control elements to allow a user to select one therefrom as his or her personal goal.

In some examples, the goal setting and analysis module 820 may generate two or more treatment and device usage goals and presented to the patient. The two or more goals may have different goal types, such as a primary sleep goal and an auxiliary mobility goal. Alternatively, the two or more goals may be of the same type but have different performance metrics, such as a primary sleep goal of sleep at least 7 hours per day, and a secondary sleep goal of keeping screen time on electronic devices such as computer, TV, smartphone, or video game console no more than 30 minutes within 2 hours prior to bedtime. The two or more treatment and device usage goals may be set to take effect in the same timeframe (the "parallel goals"). For example, a primary sleep goal of sleep 8 hours per day in 7 days can go in parallel with an mobility goal of having aerobic exercise of at least two hour per day in the same 7-day period. Alternatively, the two or more goals may be set to take effect in different timeframes (the "sequential goals") such that the completion of a first goal will automatically (or upon a user confirmation) trigger the execution of a subsequent second goal. physiological or functional information collected from the patient by the neuromodulation device 862 or other sensor devices 864 auxiliary treatment and device usage goal having a different goal type than the identified goal type of the personalized treatment and device usage goal.

The personalized treatment and device usage goal can be tracked over time by a goal tracker module 840, which can be included in or executed by the goal setting and tracking engine 716 as described above with reference to FIG. 7. The goal tracker module 840 can include a performance analyzer 842 to evaluate the patient's progress toward the personalized treatment and device usage goal over time, and a progress report generator 844 to generate a report on the tracked progress. The performance analyzer 842 can evaluate the performance metrics 824 using patient state or condition information, which may include physiological or functional information collected from the patient by the neuromodulation device 862 or other sensor devices 864 (e.g., wearables, sleep trackers, motion tracker, implantable or wearable sensors, among other devices). Based on a comparison between the evaluation of the performance metric and the personalized treatment and device usage goal, the performance analyzer 842 can categorize the patient's progress status as one of "on track", "off track", or "goal accomplished". Before reaching the end of the effective period for executing and tracking the goal, the patient is deemed "on track" if the evaluated performance metric is within a specific margin of the personalized treatment and device usage goal, or deemed "off track" if the evaluated performance metric falls out of the specific margin of the personalized treatment and device usage goal. A goal is accomplished if the evaluated performance metric stays within a specific margin of the personalized treatment and device usage goal throughout the entirety of the effective period for executing and tracking the goal. For example, to track the personalized sleep goal of "sleep at least 8 hours on average over 7 days" as shown in FIG. 8A, the performance analyzer 842 may collect patient daily sleep data from a sleep sensor or from a sleep tracker device (e.g., a sleep tracker app in a smartphone), evaluate a sleep performance metric (e.g., daily sleep duration), and determine whether the patient is on track with respect to the personalized sleep goal. In some examples, the performance analyzer 842 may generate a trend of daily sleep hours over a number of days, and predict whether the patient is on track with respect to the personalized sleep goal based on the trended sleep hours. For example, the patient is deemed on track if the average daily sleep hours is within a specific margin (e.g., +/−0.5 hour) around the personalized sleep goal of 8 hours per day, or if the patient has achieved 8-hour daily sleep in X % (e.g., 90%) of the time since the beginning of set goal. Conversely, the patient is deemed off track if the average daily sleep hours is outside the specific margin, or if the patient has failed to achieve 8-hour daily sleep in X % of time. The performance analyzer 842 can similarly track a personalized mobility goal as shown in FIG. 8B, or a personalized device usage goal as shown in FIG. 8C, based on the physiological or functional data collected by the neuromodulation device 862 or other sensor devices 864.

The patient state or condition information used by the performance analyzer 842 to evaluate the performance metrics 824 may additionally or alternatively include user feedback on execution of the personalized treatment and device usage goal. The user feedback may be provided in a form of freeform text or voices via a user-interface device. For example, the user feedback may include patient answers to a questionnaire about execution of the personalized treatment and device usage goal, or an interactive questions and answers session (e.g., an automated chatbot session) on the user interface. The sequential nature of the questions and answers encourages the patient to provide specific, focused responses about their physiological condition or the effectiveness of neuromodulation treatment. The text content may indicate or relate to the state or the condition of a patient during the execution of the personalized treatment and device usage goal, such as with text content originating from conversations or feedback received from the patient. As described above, the text content can originate from at least one of: text provided in a text chat session (e.g., transcript text) conducted between a chatbot and the patient; a voice chat session conducted between a virtual agent and the patient, with at least a portion of the voice chat session converted to text (e.g., a transcript of the chat session conversation); a text message session conducted between a text service and the patient (e.g., a transcript of one or more SMS text conversations); or an audio recording of a discussion conducted between the patient and a human agent, with at least a portion of the audio recording converted to text (e.g., a transcript of the audio recording); or a freeform text input provided by the patient (e.g., survey or question responses, narrations, etc.). The text or voice input or feedback can be processed using a NLP engine or other text analysis methods as described above with reference to FIG. 7. In some examples, multiple questions and answers sessions may be conducted over period of days, weeks, and months to allow the patient to provide updated information or additional details about his or her state or condition. Detailed description of interpreting patient text or voice input, and producing useful outcomes for diagnosis, treatment, and remediation relevant to neuromodulation therapy and device operation are disclosed in U.S. Provisional Patent Application 63/287,828, the disclosure of which are incorporated herein by reference in its entirety. The performance analyzer 842 can evaluate the performance metric 824 based on the interpretation of the patient's text or voice input or feedback, and categorize the patient's progress status as one of "on track", "off track", or "goal accomplished" with respect to the personalized treatment and device usage goal. For example, to track the personalized sleep goal of "sleep at least 8 hours on average over 7 days" as shown in FIG. 8A, the performance analyzer 842 may evaluate a sleep performance metric (e.g., daily sleep duration) based on the content extracted from patient freeform text feedback "I slept 7 hours last night", and determine whether the patient is on track with respect to the personalized sleep goal. The performance analyzer 842 can similarly track a personalized mobility goal as shown in FIG. 8B, or a personalized device usage goal as shown in FIG. 8C, based on the interpretation of the patient's text or voice input.

The progress report generator 844 can generate a report or a notification on patient progress status toward the personalized treatment and device usage goal, such as an indication of one of "on track", "off track", or "goal accomplished". The report or notification can be provided to the user (e.g., the patient or the clinician) in one or more forms, such as text messages, sounds, vibration notifications, etc. A graphical representation of the progress toward the personalized treatment and device usage goal may be displayed on a user interface. For example, FIG. 8A illustrates a user interface 850A depicting a sleep diagram 851A of daily sleep hours against the set sleep goal (8 hours), a notification of the progress status (e.g., "You are on track. Way to go with your goal!"), and a progress bar 852A indicating the percentage (e.g., 80%) of completion of the 7-day sleep goal. A user interface 850B in FIG. 8B depicts an activity diagram 851B of daily steps against the set daily step goal (3000 steps), a notification of the progress status (e.g., "You seem to have trouble keeping on track."), and a progress bar 852B indicating the percentage (e.g., 70%) of completion of the 30-day mobility goal. A user interface 850C in FIG. 8C depicts an activity diagram 851C of device charging information (e.g., power percentage before charging, data of charging, etc.), a notification 852C of goal completion status (e.g., "Congratulations! You have completed your charging goal."). An in-app badge or certificate may be given to the patient to recognize their completion of the goal. In some examples, a notification or alert on patient progress status toward the personalized treatment and device usage goal can be automatically forwarded to a clinician or other authorized users. The clinician or the authorized user may provide instructions, inquiries, or suggestions to the patient to help them keep on track on the personalized treatment and device usage goal, or adjust the goal if necessary.

The user interfaces 850A, 850B, and 850C may each include UI controls (e.g., buttons, toggle switches, actionable icons or symbols, etc.) to allow the patient to adjust or reset the personalized treatment and device usage goal, or to reprogram the device therapy. As illustrated, an "Adjust Goal" button 853 may be activated to adjust the current treatment and device usage goal if the patient is off track or to set a new goal if the patient has accomplished the presently set goal, and an "Adjust Treatment" button 854 may be activated to adjust current neuromodulation treatment such as switching to a different stimulation program or tuning a stimulation parameter. The user interfaces may include a "Help Line" 855 to allow the patient to reach out to the clinician or device expert for any inquiries about the device usage and therapy programming. In some examples, such UI control elements and the associated functionalities can be customizable such that they are displayed and become activatable only when the patient is not on track to achieve the personalized treatment and device usage goal. By way of example, operational parameters of a neuromodulation device may include amplitude, frequency, duration, pulse width, pulse type, patterns of neurostimulation pulses, waveforms in the patterns of pulses, and like settings with respect to the intensity, type, and location of neurostimulator output on individual or a plurality of respective leads. The neurostimulator may use current or voltage sources to provide the neurostimulator output, and apply any number of control techniques to modify the electrical simulation applied to anatomical sites or systems related to pain or analgesic effect. In various embodiments, a neurostimulator program may be defined or updated to indicate parameters that define spatial, temporal, and informational characteristics for the delivery of modulated energy, including the definitions or parameters of pulses of modulated energy, waveforms of pulses, pulse blocks each including a burst of pulses, pulse trains each including a sequence of pulse blocks, train groups each including a sequence of pulse trains, and programs of such definitions or parameters, each including one or more train groups scheduled for delivery. Characteristics of the waveform that are defined in the program may include, but are not limited to the following: amplitude, pulse width, frequency, total charge injected per unit time, cycling (e.g., on/off time), pulse shape, number of phases, phase order, interphase time, charge balance, ramping, as well as spatial variance (e.g., electrode configuration changes over time). It will be understood that based on the characteristics of the waveform itself, a program may have many parameter setting combinations that would be potentially available for use.

In some examples, if the patient is on track, the performance analyzer 842 may further analyze the tracked performance metric to identify neuromodulation treatment or patient activities correlated to or contributed to the "on track" status. For example, if it is found that the patient has made significant improvement toward the set goal during a particular time period, the performance analyzer 842 can identify patient activities taken or neuromodulation treatment used (e.g., device settings, therapy programs, stimulation parameter values) during that time period as contributing factors to the improved performance, and suggest behavior change or therapy adjustment to conform to the identified contributing factors, which may help the patient keep on track and ultimately accomplish the set goal successfully. If the patient is off track, the performance analyzer 842 may generate an alert to the user, set additional reminders or different types of reminders, prompt the user to adjust or automatically adjust the neuromodulation therapy, or to modify the set goal. For example, if the patient is found to fall behind the set sleep goal due to nighttime pain, the performance analyzer 842 may recommend titration of SCS therapy dosage during nighttime to alleviate pain, improve sleep quality, and help the patient achieve the sleep goal. Alternatively, the performance analyzer 842 may recommend a less aggressive sleep goal (e.g., a shorter daily average sleep hours, or a shorter effective period for tracking the sleep goal). If the patient is determined to have accomplished the set goal, the performance analyzer 842 may prompt the user to provide, or automatically generate, a new goal such as via the user interface 810A as described above. The new goal can be different than the goal that has been accomplished. For example, upon accomplishing an mobility goal of being able to stand for 15 minutes without feeling pain, a more aggressive new goal of standing for at least 30 minutes without feeling pain can be set via the user interface.

FIG. 9 illustrates, by way of example and not limitation, a method 900 of monitoring neuromodulation device treatment progress in a patient. The method 900 can be implemented in and executed by the data analysis computing system 650 as described above with reference to FIGS. 6 and 7.

At 910, a user input about a personalized objective of neuromodulation treatment for the patient or an intended manner of using the neuromodulation device by the patient may be received from a user-interface device, such as the patient interaction computing device 740 or other third party devices and platforms. The neuromodulation treatment objective may include symptom reduction (e.g., reduced pain), or an improved quality of life (QoL) metric, such as improved physical, personal autonomy, emotional, social, spiritual, or cognitive performances in patient daily life. The intended manner of using the neuromodulation device may include an desired schedule or frequency for charging the neuromodulation device, or a desired power usage mode for operating the neuromodulation device (e.g., a goal of limiting the time the neuromodulation device goes to hibernation mode). The user input can be in forms of text or voice input, such as freeform text input as shown in FIGS. 8A-8C.

At 920, the received user input can be processed to generate a personalized treatment and device usage goal for the patient. In an example where the user input includes freeform text, natural language processing (NLP) algorithms may be used to analyze the freeform text. The NLP algorithms may be implemented with use of a rule-based sentiment analyzer. One such example of a sentiment analyzer is the VADER (Valence Aware Dictionary for sEntiment Reasoning) model, which uses a list of lexical features (e.g., words) that are positive or negative. This model is sensitive to both polarity (positive/negative) and intensity (strength) of emotion indicated within text. Other models may be trained or turned with specific consideration of neuromodulation treatment and physiological conditions, and analysis or data values from multiple models may also be considered. Further, it will be understood that words can be masked or de-emphasized as part of the analysis. In an example, the freeform text may be analyzed using one of the methods such as keyword matching, topic modeling, or linguistic analysis to identify a goal type, such as a sleep goal type, a mobility goal, or a device usage goal. Additionally, one or more performance metrics associate with the goal type may be determined based on the NLP analysis of the freeform text. The performance metrics are quantifiable measures that may be used to evaluate progress toward the identified goal type.

In some examples, the personalized treatment and device usage goal (including the goal type and the performance metrics for the goal type) may be determined using patient history data and/or population data, such as stored in a database 880 as described above with reference to FIGS. 8A-8C. The patient history data may include information about historical neuromodulation treatments and patient responses thereto or historical operations of the neuromodulation device. The population data may include information about respective neuromodulation treatments and patient responses or respective operations of the neuromodulation device from a number of patients having similar medical conditions or similar demographics (collectively referred to as "similar patients") to the present patient setting the personalized treatment and device usage goal. The patient past or habitual performance metrics (e.g., a daily sleep duration, mobility minutes) may be identified from the patient history data and set as baseline values for such metrics. The patient goal may be interpreted using NLP algorithms, and the performance metric of the goal may be determined relative to the baseline metric values. Additionally or alternatively, a personalized performance metric for the patient may be determined to substantially commensurate with the population-based performance metric identified from the similar patients to the present patient. The personalized, quantifiable treatment and device usage goal, including the goal type and the performance metric, may be presented to a user (e.g., the patient) on a user interface, and the user may use one or more UI controls to accept, reject, or modify the personalized treatment and device usage goal.

In some examples, generation of the personalized treatment and device usage goal may be based on patient state or condition even without the patient explicitly specifying his or her treatment objective or intended device usage pattern. Such patient state or condition may be determined using physiological or functional information collected from the patient by the neuromodulation device or other sensor devices. The patient state or condition may additionally or alternatively be determined using patient input or feedback on his or her state or condition, QoL attributes, responses to neuromodulation treatment, among others. In an example, the patient input or feedback is in forms of text or voice, which can be processed using NLP algorithms other text analysis methods as described above with reference to FIG. 7.

At 930, the patient treatment and device usage goal can be tracked over time, such as using the goal tracker module 840 as described above with reference to FIGS. 8A-8C. The one or more performance metrics as determined at step 920 can be evaluated using patient state or condition information, which may include physiological or functional information collected from the patient by the neuromodulation device or other sensor devices. Based on a comparison between the evaluation of the performance metric and the personalized treatment and device usage goal, a progress status can be determined as one of "on track", "off track", or "goal accomplished" with respect to the personalized treatment and device usage goal.

In some examples, the patient state or condition information may additionally or alternatively include user feedback on execution of the personalized treatment and device usage goal. The user feedback may be provided in a form of freeform text or voices via a user-interface device. The text or voice input or feedback can be processed using a NLP engine or other text analysis methods as described above with reference to FIG. 7. performance analyzer 842 can evaluate the performance metric 824 based on the interpretation of the patient's text or voice input or feedback, and categorize the patient's progress status as one of "on track", "off track", or "goal accomplished" with respect to the personalized treatment and device usage goal.

At 940, the tracked progress can be provided to the patient or an authorized user (e.g., the clinician or a device expert). In an example, the progress status (e.g., "on track", "off track", or "goal accomplished") may be presented to the patient or the authorized user in one or more forms, such as text messages, sounds, vibration notifications, etc. In some examples, a graphical representation of the progress toward the personalized treatment and device usage goal may be displayed on a user interface, such as those examples shown in FIGS. 8A-8C. For example, when it is determined that the patient is "on track," the neuromodulation treatment or patient activities that are correlated to the "on track" determination can be identified as contributing factors to the improvement toward the set goal during a particular time period.

Recommendations for behavior change or therapy adjustment to conform to the identified contributing factors can be provided to the patient. When it is determined that the patient is "off track," an alert may be provided to the patient or an authorized user. Additional reminders or distinct types of reminders may be set for the rest of the effective period for executing and tracking the goal, or the patient may be prompted to modify the personalized treatment and device usage goal or to adjust the neuromodulation therapy. Alternatively, the personalized treatment and device usage goal or the neuromodulation therapy may be automatically adjusted. When it is determined that the patient has accomplished the set goal, the user may be notified and prompted to provide a new goal different than the goal that has been accomplished. In an example, the new goal can be more aggressive than the old goal that has been accomplished.

Depending on the progress status, a therapy parameter may be adjusted either automatically or manually by the patient or an authorized user, and neuromodulation therapy may be delivered in accordance with the adjusted therapy parameter at 950. Although many of the preceding examples were provided with reference to SCS therapy for treating or alleviating chronic pain, it will be understood that the present techniques may also be applicable to other forms of neurostimulation, such as deep brain stimulation to motor symptoms or patient motor capabilities.

FIG. 10 illustrates generally a block diagram of an example machine 1000 upon which any one or more of the techniques (e.g., methodologies) discussed herein may perform. Portions of this description may apply to the computing framework of various portions of the data analysis computing system 650, or various components of the computing system illustrated in FIGS. 8A-8C that can generate a personalized, quantifiable treatment and device usage goal and to track progress toward such goal.

In alternative embodiments, the machine 1000 may operate as a standalone device or may be connected (e.g., networked) to other machines. In a networked deployment, the machine 1000 may operate in the capacity of a server machine, a client machine, or both in server-client network environments. In an example, the machine 1000 may act as a peer machine in peer-to-peer (P2P) (or other distributed) network environment. The machine 1000 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 1000 may include a hardware processor 1002 (e.g., a central processing unit (CPU), a graphics processing unit (GPU), a hardware processor core, or any combination thereof), a main memory 1004 and a static memory 1006, some or all of which may communicate with each other via an interlink (e.g., bus) 1008. The machine 1000 may further include a display unit 1010 (e.g., a raster display, vector display, holographic display, etc.), an alphanumeric input device 1012 (e.g., a keyboard), and a user interface (UI) navigation device 1014 (e.g., a mouse). In an example, the display unit 1010, input device 1012 and UI navigation device 1014 may be a touch screen display. The machine 1000 may additionally include a storage device (e.g., drive unit) 1016, a signal generation device 1018 (e.g., a speaker), a network interface device 1020, and one or more sensors 1021, such as a global positioning system (GPS) sensor, compass, accelerometer, or other sensor. The machine 1000 may include an output controller 1028, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1016 may include a machine readable medium 1022 on which is stored one or more sets of data structures or instructions 1024 (e.g., software) embodying or utilized by any one or more of the techniques or functions described herein. The instructions 1024 may also reside, completely or at least partially, within the main memory 1004, within static memory 1006, or within the hardware processor 1002 during execution thereof by the machine 1000. In an example, one or any combination of the hardware processor 1002, the main memory 1004, the static memory 1006, or the storage device 1016 may constitute machine readable media.

While the machine readable medium 1022 is illustrated as a single medium, the term "machine readable medium" may include a single medium or multiple media (e.g., a centralized or distributed database, and/or associated caches and servers) configured to store the one or more instructions 1024.

The term "machine readable medium" may include any medium that is capable of storing, encoding, or carrying instructions for execution by the machine 1000 and that cause the machine 1000 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1024 may further be transmitted or received over a communications network 1026 using a transmission medium via the network interface device 1020 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 1020 may include one or more physical jacks (e.g., Ethernet, coaxial, or phone jacks) or one or more antennas to connect to the communications network 1026. In an example, the network interface device 1020 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1000, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for monitoring neuromodulation device treatment progress of a patient, the system comprising:

a user-interface device; and a controller circuit configured to:

receive from the user-interface device a user input about (i) a personalized objective of neuromodulation treatment for the patient or (ii) an intended manner of using the neuromodulation device by the patient;

process the user input to generate a personalized treatment and device usage goal comprising at least one of a quality-of-life functional goal, a device-usage preference, or a charging-behavior goal;

track progress toward the personalized treatment and device usage goal based on patient state information; and generate a control signal to the neuromodulation device to initiate or adjust a neuromodulation therapy based on the tracked progress toward the personalized treatment and device usage goal.

2. The system of claim 1, wherein the user input includes text or voice input, and wherein to generate the personalized treatment and device usage goal, the controller circuit is configured to process the text or voice input using natural language processing, and to generate the personalized treatment and device usage goal based on the processed text or voice input.

3. The system of claim 2, wherein to generate the personalized treatment and device usage goal, the controller circuit is configured to determine a goal type using topic modeling of the text or voice input, and to generate a performance metric for the determined goal type.

4. The system of claim 3, wherein the controller circuit is configured to evaluate the performance metric using the patient state information, and to track the progress toward the personalized treatment and device usage goal based on the evaluation of the performance metric.

5. The system of claim 4, wherein the controller circuit is configured to determine that the patient is on track, off track, or has achieved the personalized treatment and device usage goal based on a comparison between the evaluated performance metric and the personalized treatment and device usage goal.

6. The system of claim 5, wherein, in response to the determination that the patient is on track, the controller circuit is configured to:

Identify a neuromodulation treatment or patient activities correlated to the determination of the patient being on track; and present information about the identified neuromodulation treatment or the patient activities on the user-interface device.

7. The system of claim 5, wherein, in response to the determination that the patient is off track, the controller circuit is configured to:

generate an alert to the patient; and automatically modify or prompt the patient to modify the personalized treatment and device usage goal or to adjust the neuromodulation therapy.

8. The system of claim 5, wherein, in response to the determination that the patient has achieved the personalized treatment and device usage goal, the controller circuit is configured to automatically generate or prompt the user to provide another goal different than the personalized treatment and device usage goal that has been achieved.

9. The system of claim 1, wherein the patient state information used for tracking the progress toward the personalized treatment and device usage goal includes at least one of physiological or functional information of the patient collected by one or more sensors, or a text or voice feedback on execution of the personalized treatment and device usage goal provided by a user via the user-interface device.

10. The system of claim 1, wherein the controller circuit is configured to generate or modify the personalized treatment and device usage goal further using historical data of the patient in relation to historical neuromodulation treatments and patient responses thereto or historical manners of operating the neuromodulation device.

11. The system of claim 1, wherein the controller circuit is configured to generate or modify the personalized treatment and device usage goal further using population-based data collected from a plurality of individuals having similar medical conditions or similar demographics to the patient, the population-based data in relation to neuromodulation treatments and patient responses thereto or manners of operating respective neuromodulation devices.

12. The system of claim 1, wherein the personalized treatment and device usage goal includes at least one of:

a mobility goal;

a sleep goal;

a pain relief goal; or an emotion goal.

13. The system of claim 1, wherein the personalized treatment and device usage goal includes at least one of:

a device charging schedule or frequency; or a power usage mode of the neuromodulation device.

14. A method of monitoring neuromodulation device treatment progress in a patient, the method comprising:

receiving from a user-interface device a user input about (i) a personalized objective of neuromodulation treatment for the patient or (ii) an intended manner of using the neuromodulation device by the patient;

generating, via a controller circuit, a personalized treatment and device usage goal using the received user input, the device usage goal comprising at least one of a quality-of-life functional goal, a device-usage preference, or a charging-behavior goal;

tracking, via the controller circuit, progress toward the personalized treatment and device usage goal based on patient state information; and initiating or adjusting a neuromodulation therapy via the neuromodulation device based on the tracked progress toward the personalized treatment and device usage goal.

15. The method of claim 14, wherein the user input includes text or voice input, wherein generating the personalized treatment and device usage goal includes processing the text or voice input using natural language processing, and generating the personalized treatment and device usage goal based on the processed text or voice input.

16. The method of claim 15, wherein generating the personalized treatment and device usage goal includes determining a goal type using topic modeling of the text or voice input, and generating a performance metric for the determined goal type.

17. The method of claim 16, comprising evaluating the performance metric using the patient state information, wherein tracking the progress toward the personalized treatment and device usage goal is based on the evaluation of the performance metric.

18. The method of claim 17, comprising determining that the patient is on track, off track, or has achieved the personalized treatment and device usage goal based on a comparison between the evaluated performance metric and the personalized treatment and device usage goal.

19. The method of claim 14, wherein the patient state information used for tracking the progress toward the personalized treatment and device usage goal includes at least one of physiological or functional information of the patient collected by one or more sensors, or a text or voice feedback on execution of the personalized treatment and device usage goal provided by a user via the user-interface device.

20. The method of claim 14, wherein generating the personalized treatment and device usage goal is further based on at least one of:

historical data of the patient in relation to historical neuromodulation treatments and patient responses thereto or historical manners of operating of the neuromodulation device; or population-based data collected from a plurality of individuals having similar medical conditions or similar demographics to the patient, the population-based data in relation to neuromodulation treatments and patient responses thereto or manners of operating respective neuromodulation devices.

* * * * *